(12) United States Patent
Hart et al.

(10) Patent No.: US 7,699,870 B2
(45) Date of Patent: Apr. 20, 2010

(54) SURGICAL FASTENING SYSTEM AND METHOD FOR USING THE SAME

(75) Inventors: Rickey D. Hart, Plainville, MA (US); John T. Rice, Lincoln, MA (US)

(73) Assignee: Ethicon, Inc., Somerville, NJ (US)

( * ) Notice: Subject to any disclaimer, the term of this patent is extended or adjusted under 35 U.S.C. 154(b) by 573 days.

(21) Appl. No.: 11/520,002

(22) Filed: Sep. 12, 2006

(65) Prior Publication Data

US 2007/0073336 A1 Mar. 29, 2007

Related U.S. Application Data

(63) Continuation of application No. 09/875,588, filed on Jun. 6, 2001, now Pat. No. 7,105,010, which is a continuation of application No. 09/340,584, filed on Jun. 28, 1999, now abandoned, which is a continuation of application No. 09/174,814, filed on Oct. 19, 1998, now abandoned, which is a continuation of application No. 08/560,111, filed on Nov. 17, 1995, now Pat. No. 5,827,298.

(51) Int. Cl.
A61B 17/08 (2006.01)
A61B 17/58 (2006.01)

(52) U.S. Cl. ............ 606/213; 606/104; 606/220

(58) Field of Classification Search ............ 606/213, 606/220, 104, 148; 604/59–61; 128/831
See application file for complete search history.

(56) References Cited

U.S. PATENT DOCUMENTS

| | | |
|---|---|---|
| 3,166,072 A | 1/1965 | Sullivan |
| 3,675,639 A * | 7/1972 | Cimber ............ 128/831 |
| 3,716,058 A | 2/1973 | Tanner, Jr. |
| 3,946,740 A | 3/1976 | Bassett |
| 3,981,051 A | 9/1976 | Brumlik |
| 4,006,747 A | 2/1977 | Kronenthal et al. |
| 4,060,089 A | 11/1977 | Noiles |
| 4,144,876 A | 3/1979 | DeLeo |
| 4,259,959 A | 4/1981 | Walker |
| 4,316,469 A | 2/1982 | Kapitanov |
| 4,532,926 A | 8/1985 | O'Holla |
| 4,548,202 A | 10/1985 | Duncan |
| 4,627,437 A | 12/1986 | Bedi et al. |
| 4,635,637 A | 1/1987 | Schreiber |
| 4,669,473 A | 6/1987 | Richards et al. |
| 4,688,561 A | 8/1987 | Reese |
| 4,705,040 A | 11/1987 | Mueller et al. |
| 4,736,746 A | 4/1988 | Anderson |
| 4,873,976 A | 10/1989 | Schreiber |
| 4,884,572 A | 12/1989 | Bays et al. |
| 4,895,148 A | 1/1990 | Bays et al. |
| 4,899,743 A | 2/1990 | Nicholson et al. |
| 4,924,865 A | 5/1990 | Bays et al. |
| 4,935,028 A | 6/1990 | Drews |

(Continued)

FOREIGN PATENT DOCUMENTS

DE 2740274 3/1978

(Continued)

*Primary Examiner*—Julian W Woo

(57) ABSTRACT

A surgical fastening system for attaching one piece of tissue to another piece of tissue. The system comprises a surgical fastener, an installation tool for deploying the surgical fastener in tissue, and a method for using the same.

6 Claims, 34 Drawing Sheets

U.S. PATENT DOCUMENTS

| | | |
|---|---|---|
| 4,943,294 A | 7/1990 | Knapp |
| 4,976,715 A | 12/1990 | Bays et al. |
| 5,013,316 A | 5/1991 | Goble et al. |
| 5,053,047 A | 10/1991 | Yoon |
| 5,059,206 A | 10/1991 | Winters |
| 5,085,661 A | 2/1992 | Moss |
| 5,129,906 A | 7/1992 | Ross et al. |
| 5,246,441 A | 9/1993 | Ross et al. |
| 5,312,360 A | 5/1994 | Behl |
| 5,370,646 A | 12/1994 | Reese et al. |
| 5,380,290 A | 1/1995 | Makower et al. |
| 5,433,722 A * | 7/1995 | Sharpe et al. ............... 606/148 |
| 5,470,337 A | 11/1995 | Moss |
| 5,562,704 A | 10/1996 | Tamminmaki et al. |
| 5,569,264 A | 10/1996 | Tamminmaki et al. |
| 5,827,298 A | 10/1998 | Hart et al. |

FOREIGN PATENT DOCUMENTS

| | | |
|---|---|---|
| FR | 2573647 | 5/1986 |
| JP | 58160013 | 9/1983 |
| JP | 60012047 | 1/1985 |
| JP | 60012049 | 1/1985 |
| JP | 06502791 | 3/1994 |
| WO | 9208513 | 5/1992 |

* cited by examiner

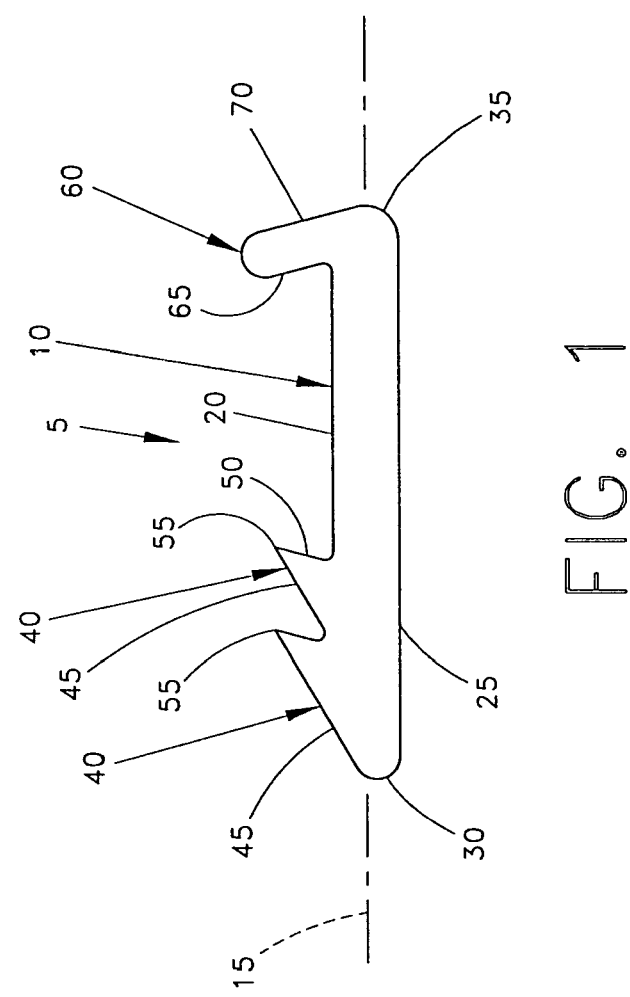
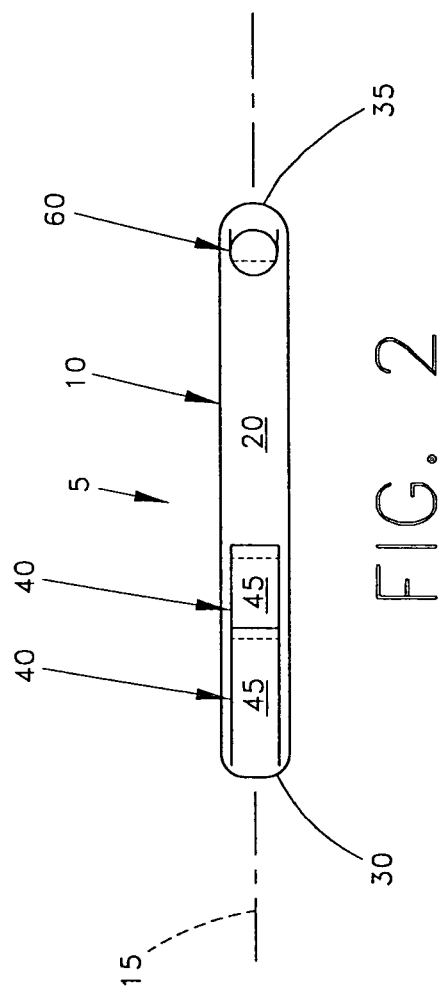
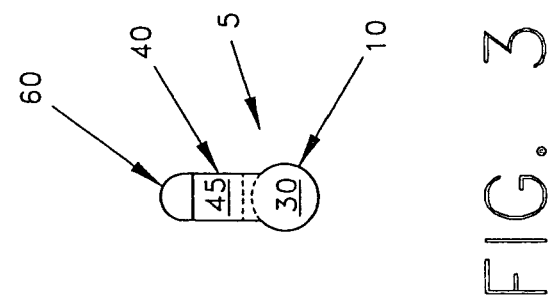

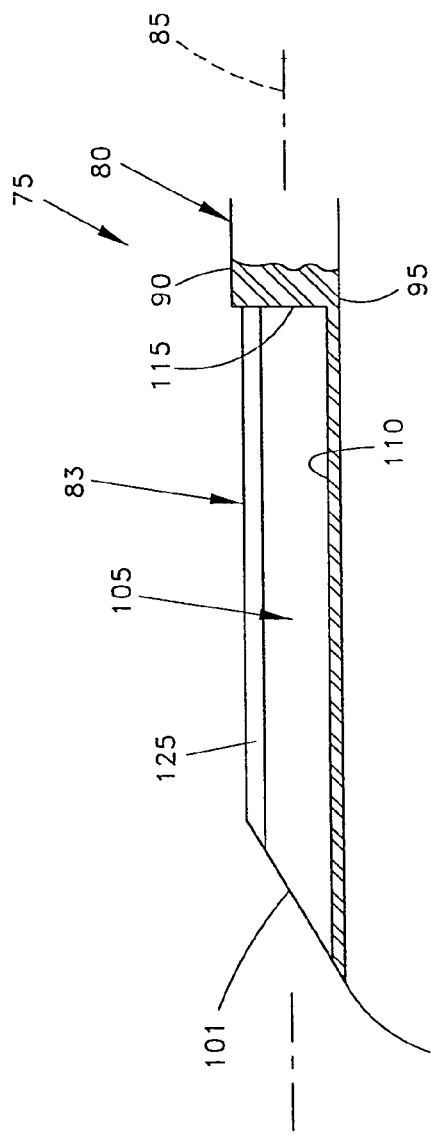
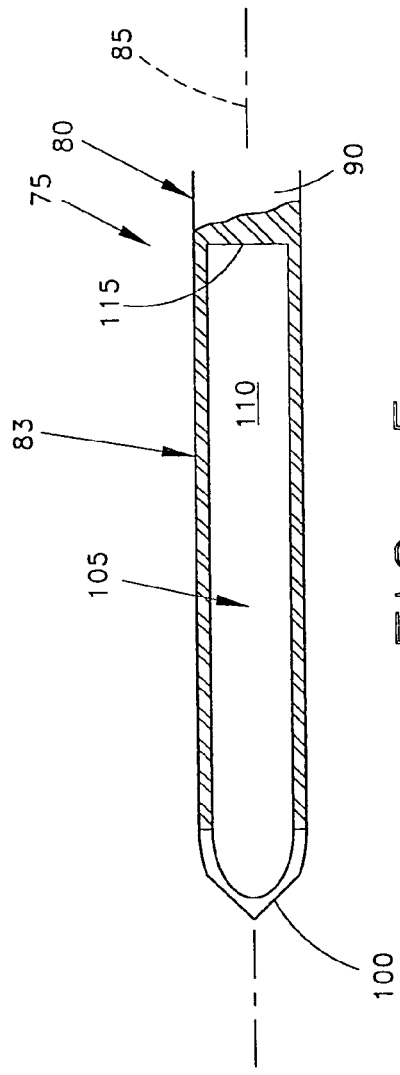
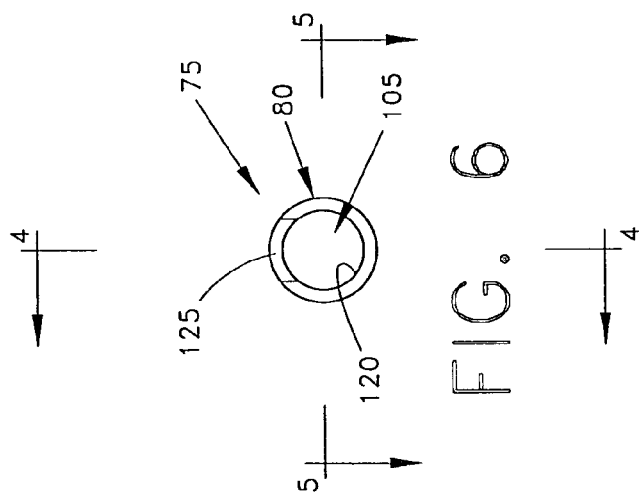

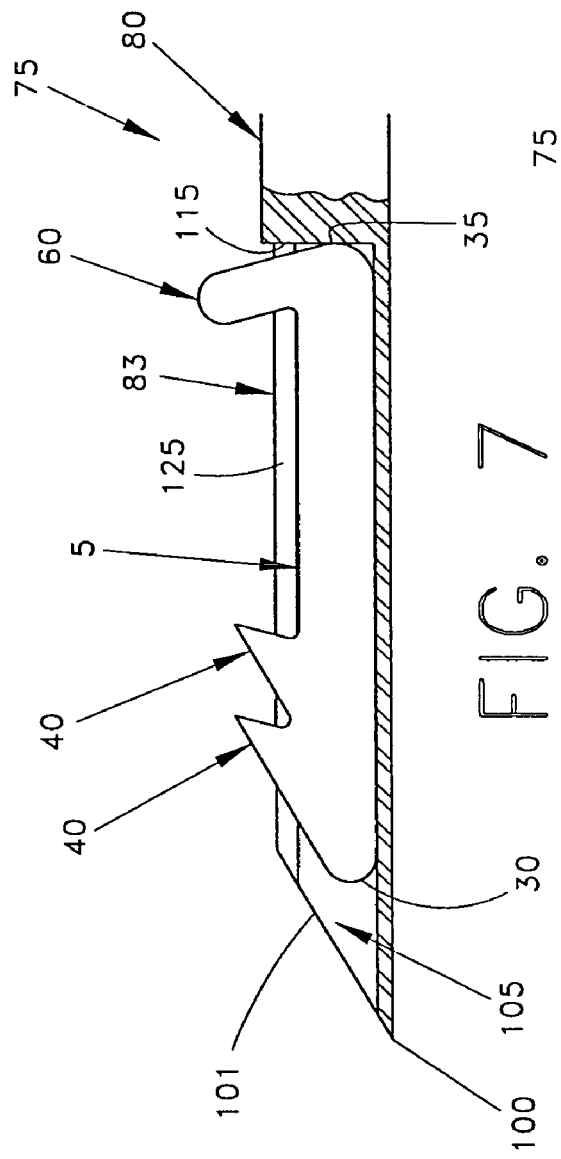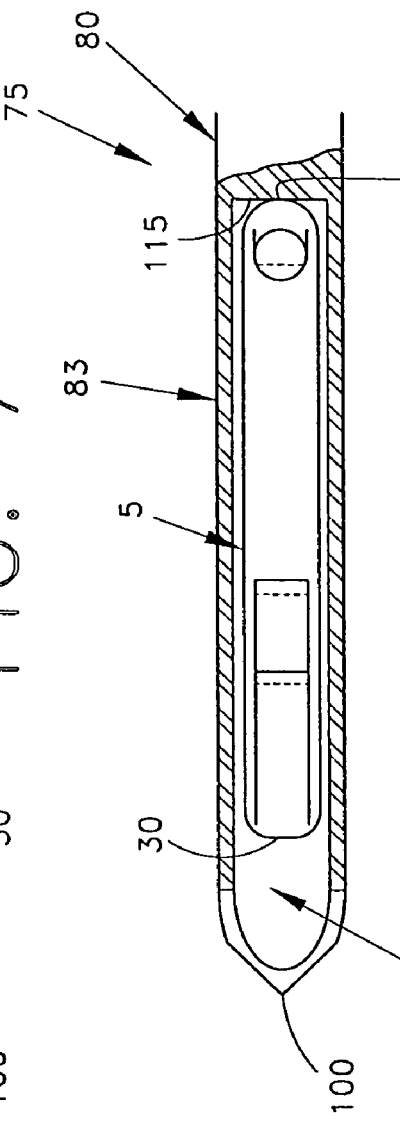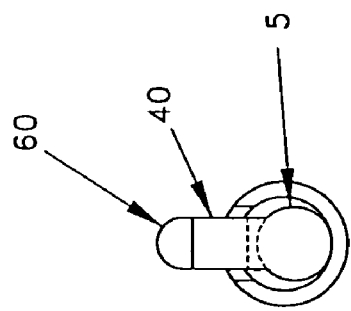

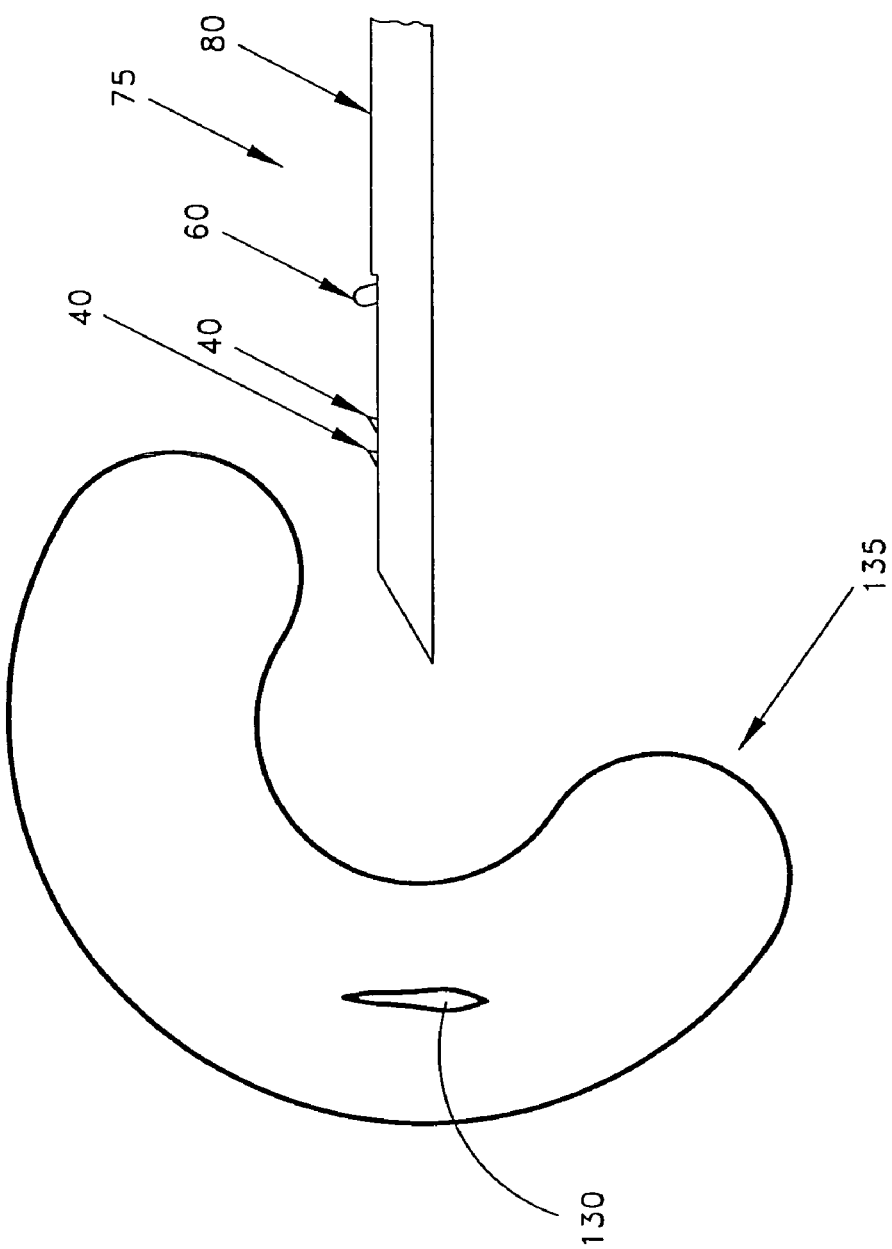

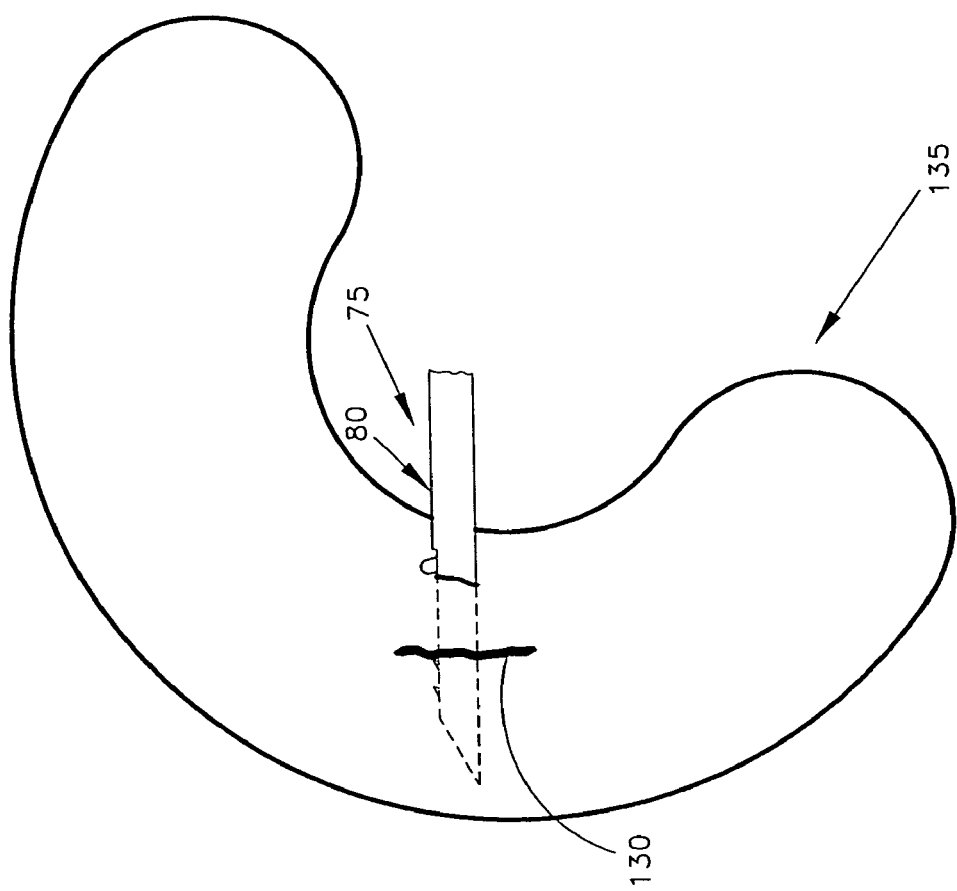

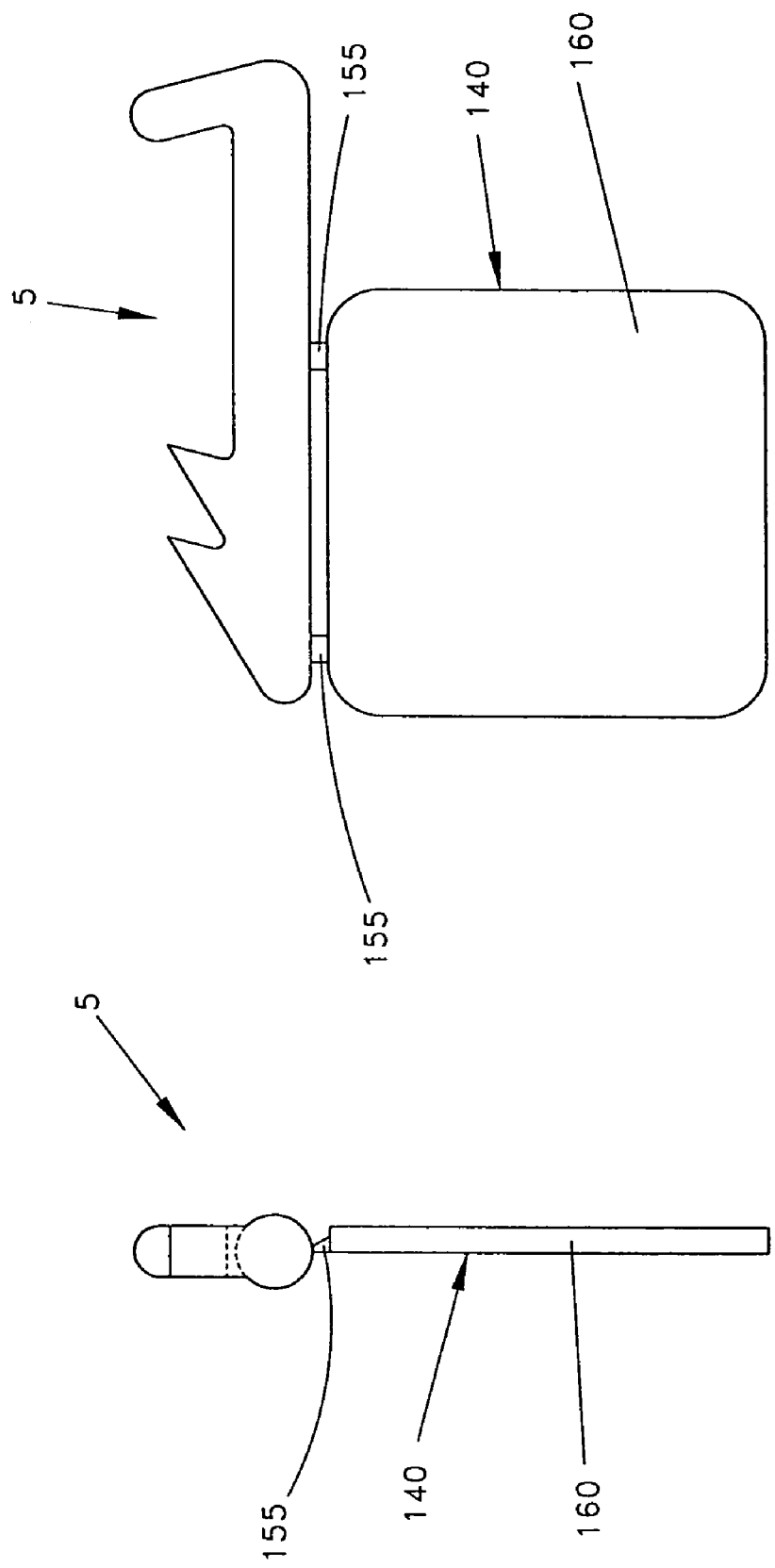

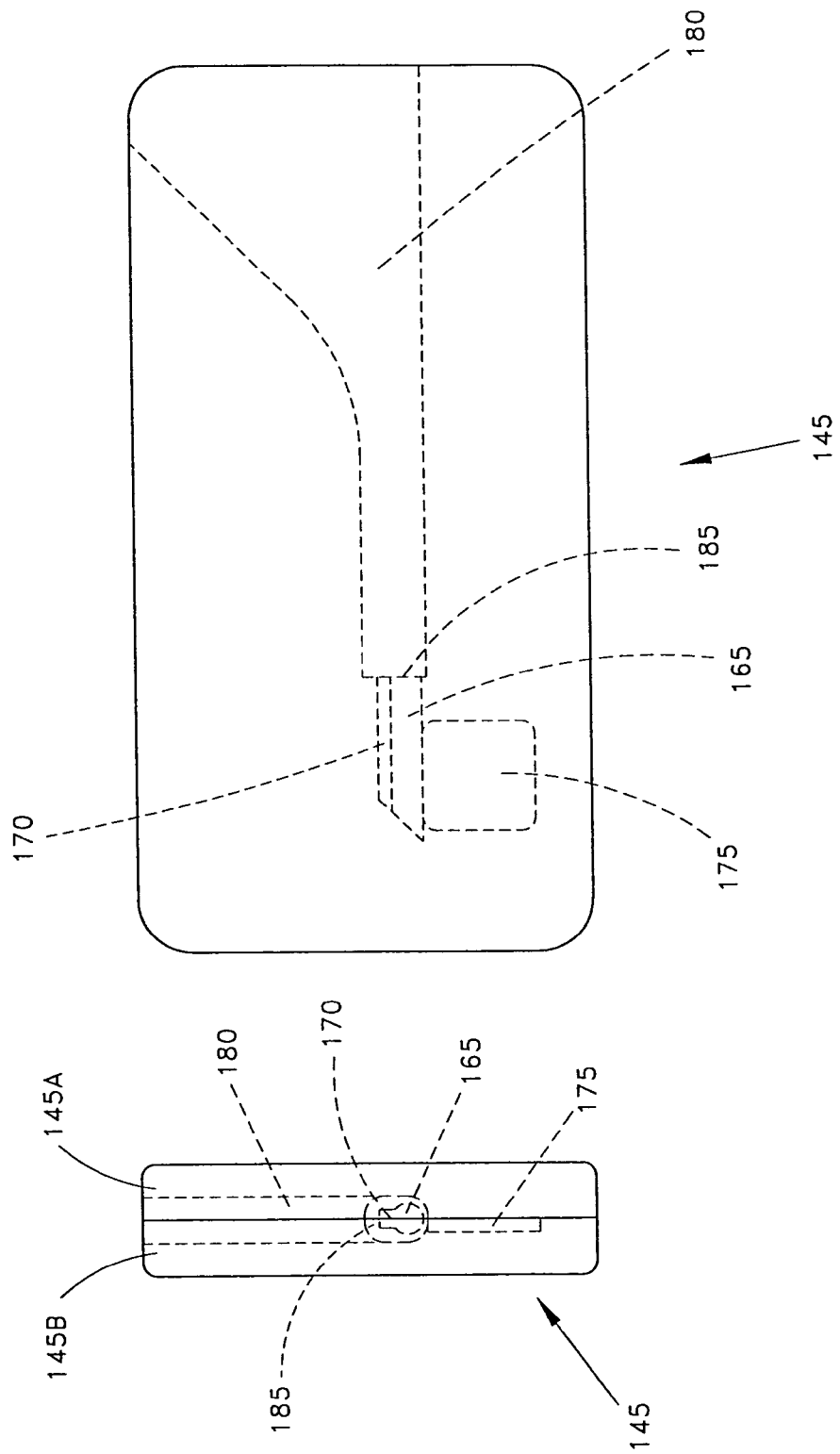

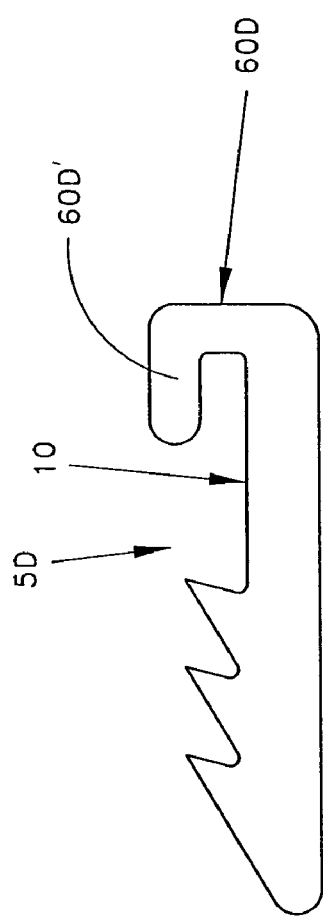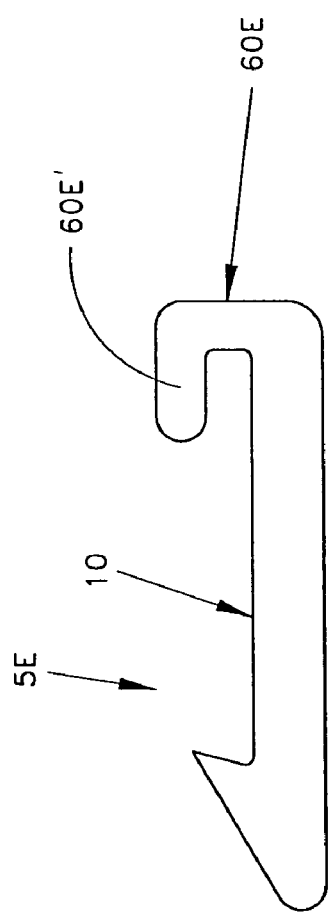

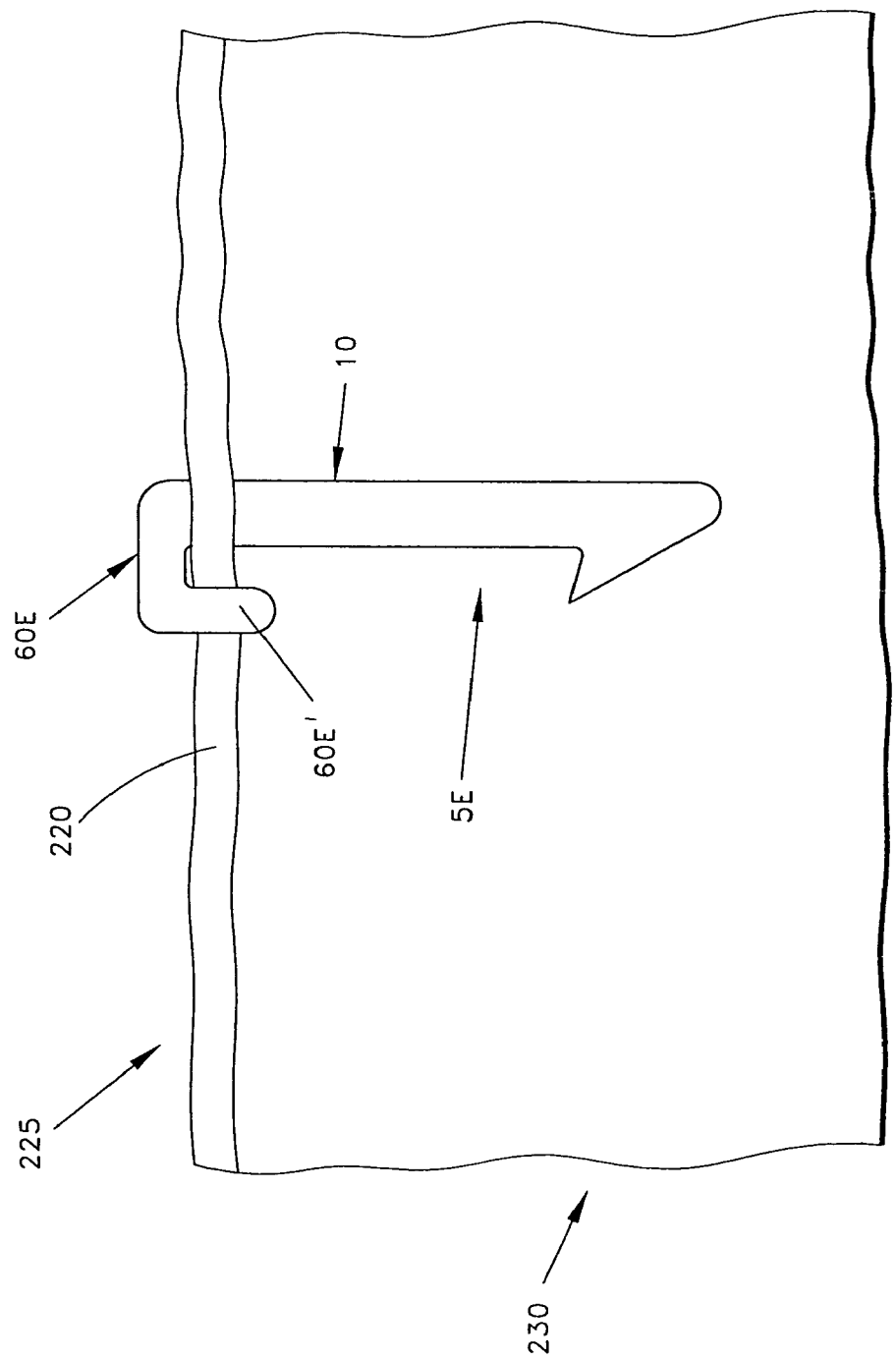

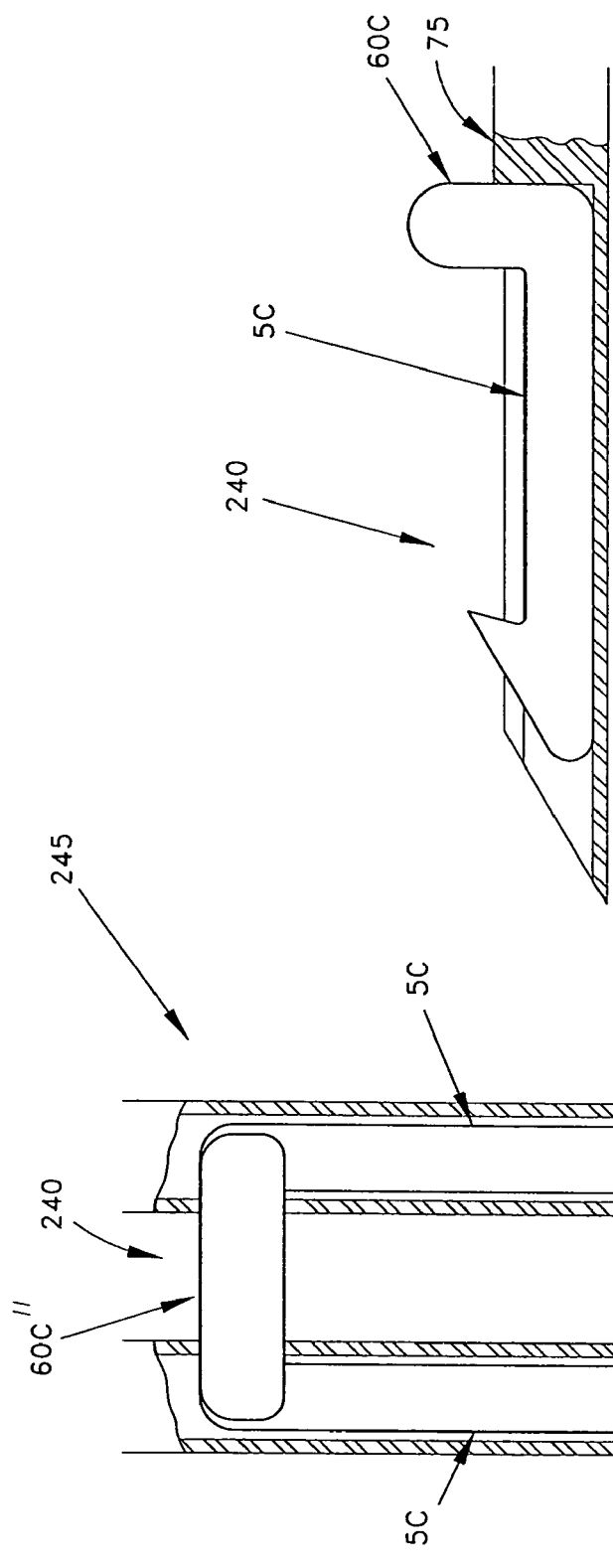

SURGICAL FASTENING SYSTEM AND METHOD FOR USING THE SAME

REFERENCE TO PENDING PRIOR PATENT APPLICATIONS

This patent application is a continuation of prior U.S. patent application Ser. No. 09/875,588, filed Jun. 6, 2001 now U.S. Pat. No. 7,105,010 by Rickey D. Hart et al. for SURGICAL FASTENING SYSTEM AND METHOD FOR USING THE SAME, which is in turn a continuation of prior U.S. patent application Ser. No. 09/340,584, filed Jun. 28, 1999 now abandoned by Rickey D. Hart et al. for SURGICAL FASTENING SYSTEM AND METHOD FOR USING THE SAME, which is in turn a continuation of prior U.S. patent application Ser. No. 09/174,814, filed Oct. 19, 1998 now abandoned by Rickey D. Hart et al. for SURGICAL FASTENING SYSTEM AND METHOD FOR USING THE SAME and which is in turn a continuation of prior U.S. patent application Ser. No. 08/560,111, filed Nov. 17, 1995 now U.S. Pat. No. 5,827,298 by Rickey D. Hart et al. for SURGICAL FASTENING SYSTEM AND METHOD FOR USING THE SAME.

The above-identified patent applications are hereby incorporated herein by reference.

FIELD OF THE INVENTION

This invention relates to surgical fastening systems in general, and more particularly to surgical fastening systems of the sort comprising tack-like fasteners for attaching one piece of tissue to another piece of tissue.

BACKGROUND OF THE INVENTION

In many medical applications, it is necessary (or at least desirable) to fasten one piece of tissue to another piece of tissue.

In the case of soft tissue, this fastening is traditionally accomplished by sewing the two pieces of tissue together using needle and suture.

Unfortunately, in certain situations it can be extremely difficult, or even impossible, to suture two pieces of tissue together. In many cases this is due to the natural constraints imposed by the patient's anatomical structure. By way of example, it can be extremely difficult to suture meniscal cartilage, which is located within the interior of the knee joint. Unfortunately, this presents a serious problem, inasmuch as many injuries involve tears to the meniscal cartilage, and suturing would provide an otherwise preferred manner of repair.

With this and other situations in mind, a variety of different surgical fastening systems have been developed to replace, or at least supplement, conventional suturing.

See, for example, U.S. Pat. Nos. 3,716,058 (Tanner, Jr.); 4,532,926 (O'Halla); 4,548,202 (Duncan); 4,635,637 (Schreiber); 4,669,473 (Richards et al.); 4,873,976 (Schreiber); 4,884,572 (Bays et al.); 4,895,148 (Bays et al.); 4,924,865 (Bays et al.); 4,976,715 (Bays et al.); 5,053,047 (Yoon); and 5,059,206 (Winters); French Patent Publication No. 2,573,647 (Catier); and Japanese Patent Publication No. 58-160013.

See also, for example, U.S. Pat. Nos. 4,688,561 (Reese); 4,935,028 (Drews); 5,013,316 (Goble et al.); 5,129,906 (Ross et al.); 5,246,441 (Ross et al.); and 5,370,646 (Reese et al.).

Unfortunately, none of the prior art surgical fastening systems have proven to be entirely satisfactory, for a wide variety of different reasons. The inadequacy of prior art surgical fastening systems has proven to be particularly significant with respect to repairing tears in meniscal cartilage within the interior of the knee joint.

OBJECTS OF THE INVENTION

Accordingly, one object of the present invention is to provide a novel surgical fastening system for attaching one piece of tissue to another piece of tissue, wherein the novel surgical fastening system overcomes the various deficiencies associated with prior art surgical fastening systems.

Another object of the present invention is to provide a novel surgical fastener for attaching one piece of tissue to another piece of tissue.

Still another object of the present invention is to provide a novel installation tool for deploying the aforementioned surgical fastener in tissue.

Yet another object of the present invention is to provide a novel surgical fastening system which is particularly well suited for use in repairing tears in meniscal cartilage.

And another object of the present invention is to provide a novel surgical fastener which is particularly well suited for use in repairing tears in meniscal cartilage.

And still another object of the present invention is to provide a novel installation tool which is particularly well suited for use in deploying the aforementioned surgical fastener in meniscal cartilage.

And yet another object of the present invention is to provide a novel method for fastening one piece of tissue to another piece of tissue.

And still another object of the present invention is to provide a novel method for repairing tears in meniscal cartilage.

SUMMARY OF THE INVENTION

These and other objects are addressed by the present invention, which comprises a surgical fastening system and a method for using the same.

The surgical fastening system generally comprises a novel surgical fastener and a novel installation tool.

The novel surgical fastener generally comprises a solid shaft of substantially uniform diameter having a distal end and a proximal end; a bar at the proximal end of the shaft, the bar extending outwardly from the shaft; the distal end of the shaft being rounded and devoid of a cutting edge and devoid of a penetration point; and a fin extending outwardly from the shaft proximate the distal end, the fin having a distal edge inclined outwardly and proximally from the shaft and a proximal edge inclined outwardly and proximally from the shaft.

The novel installation tool generally comprises an elongated inserter which includes a carrier portion, the carrier portion being adapted to retain the fastener and having at a distal end thereof a sharpened edge, the carrier portion having an open side from which extend end portions of the fastener's bar and fin.

The surgical fastening system is generally used as follows. First, the surgical fastener is fitted to the installation tool's carrier portion so that the end portions of the fastener's bar and fin protrude from the carrier portion's open side. Then the installation tool is manipulated so that its carrier portion and the surgical fastener are projected into tissue, until the protruding portion of the fastener's bar engages the outer surface of the tissue. Finally, the installation tool is manipulated so that the installation tool's carrier portion is withdrawn from the tissue, whereupon the protruding portion of the fastener's fin resists proximal movement of the fastener, causing the fastener to be left in the tissue.

In order to facilitate initial handling of the surgical fastener and loading the fastener into the installation tool's carrier portion, the surgical fastener may initially be connected to a grip by one or more tabs, and the surgical fastener and its associated grip may initially be loaded into a holder, with the fastener being accessible in the holder through an opening. Thereafter, the surgical fastener can be loaded into the installation tool's carrier portion by inserting the distal end of the installation tool into the holder's opening, whereby the distal end of the installation tool will serially sever any tabs holding the surgical fastener to the grip as the surgical fastener is simultaneously loaded into the installation tool's carrier portion. The installation tool and the surgical fastener can thereafter be withdrawn from the holder as a unit, ready for use in attaching one piece of tissue to another piece of tissue.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 1 is a side view of a surgical fastener formed in accordance with the present invention;

FIG. 2 is a top view of the same surgical fastener;

FIG. 3 is a front end view of the same surgical fastener;

FIG. 4 is a partial side view, partially in section, of an installation tool formed in accordance with the present invention, with the view having been taken along line 4-4 in FIG. 6;

FIG. 5 is a partial top view, partially in section, of the same installation tool, with the view having been taken along line 5-5 in FIG. 6;

FIG. 6 is a front end view of the same installation tool;

FIG. 7 is a partial side view, partially in section, showing the surgical fastener of FIGS. 1-3 loaded into the installation tool of FIGS. 4-6;

FIG. 8 is a partial top view, partially in section, of the assembly shown in FIG. 7;

FIG. 9 is a front end view of the assembly shown in FIGS. 7 and 8;

FIG. 10 is a schematic view showing the assembly of FIGS. 7-9 approaching a tear located in a piece of meniscal cartilage;

FIG. 11 is a schematic view showing the assembly of FIGS. 7-9 spanning the aforementioned tear;

FIG. 13 is side view of the same surgical fastener shown in FIGS. 1-3, wherein the fastener is shown attached to a grip by a pair of tabs;

FIG. 14 is a front end view of the same surgical fastener and its associated grip;

FIG. 15 is a side view of a holder for holding the surgical fastener and its associated grip prior to loading the surgical fastener into its associated installation tool;

FIG. 16 is a rear end view of the same holder, i.e., as seen from the right side in FIG. 15;

FIG. 33 is a side view of a fifth surgical fastener formed in accordance with the present invention;

FIG. 34 is a side view of a sixth surgical fastener formed in accordance with the present invention;

FIG. 35 is a side view showing the surgical fastener of FIG. 34 attaching a piece of surgical mesh to a piece of tissue;

FIG. 39 is a partial side view, partially in section, of an assembly comprising a seventh surgical fastener formed in accordance with the present invention and an installation tool for deploying the same;

FIG. 40 is a partial top view, partially in section, of the assembly shown in FIG. 39;

DETAILED DESCRIPTION OF THE PREFERRED EMBODIMENTS

Figure 12:
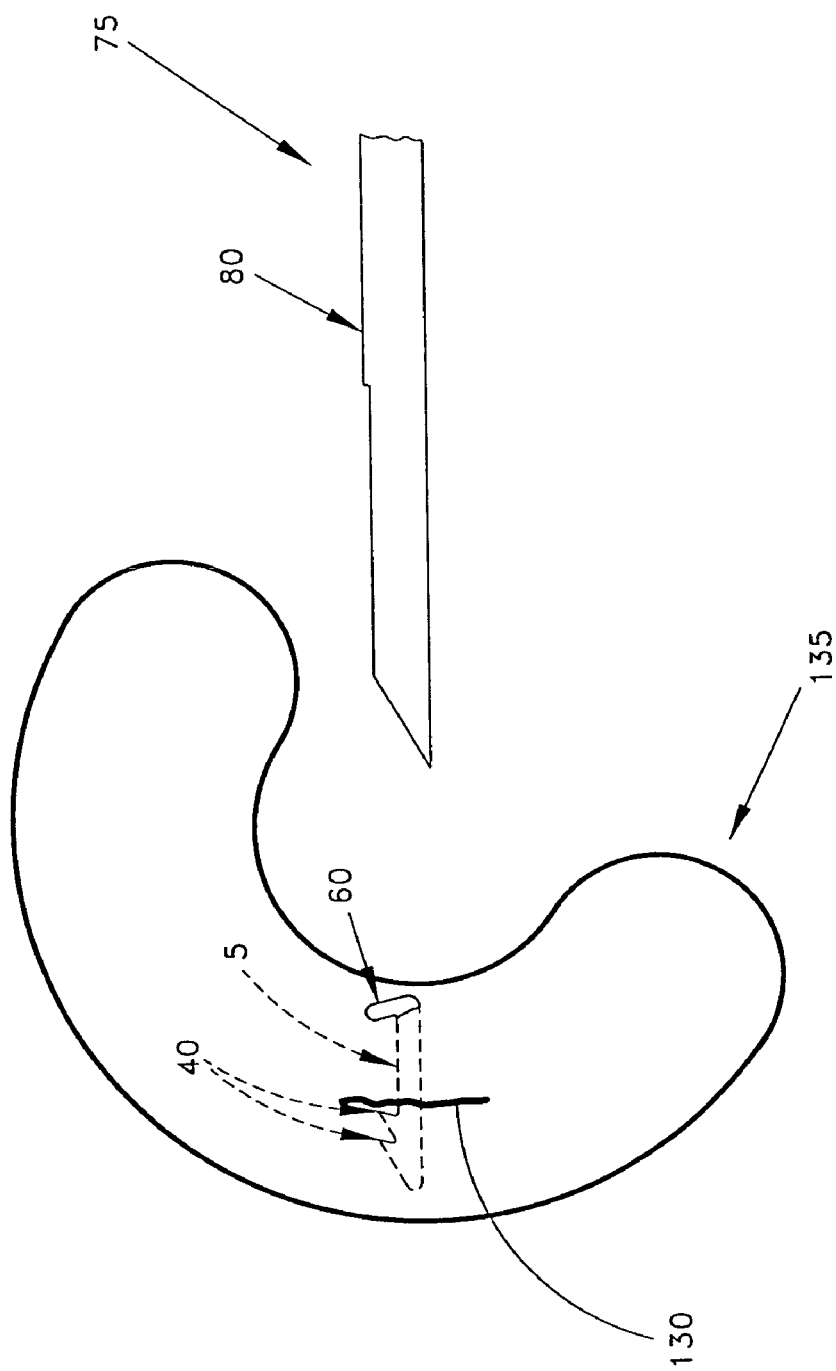
FIG. 12 is a schematic view showing the surgical fastener of FIGS. 1-3 holding the aforementioned tear closed as the fastener's associated installation tool is withdrawn from the piece of meniscal cartilage.

Looking first at FIGS. 1-3, there is shown a surgical fastener 5 which is formed in accordance with the present invention. Surgical fastener 5 comprises a shaft 10 extending along a longitudinal axis 15 and having a top surface 20, a bottom surface 25, a distal end surface 30 and a proximal end surface 35. Distal end surface 30 is formed so as to have a blunt configuration, devoid of a cutting edge and devoid of a penetration point. Preferably distal end surface 30 is formed so as to have a substantially rounded configuration, for reasons which will hereinafter be disclosed in further detail. Proximal end surface 35 is preferably also formed so as to have a rounded configuration, for reasons which will hereinafter be disclosed in further detail.

At least one fin 40 extends out of the fastener's top surface 20, adjacent to distal end surface 30. Each fin 40 is configured so as to (i) present the least possible resistance to tissue when the fastener is being passed, distal end first, through tissue, and (ii) present the greatest possible resistance to tissue when the fin is being withdrawn, proximal end first, from tissue. To this end, each fin 40 generally projects radially outwardly, and longitudinally rearwardly, from shaft 10. Preferably each fin 40 comprises a leading surface 45 and a trailing surface 50, where leading surface 45 is disposed at a significantly more acute angle to the shaft's longitudinal axis 15 than trailing surface 50. By way of example, leading surface 45 might be disposed at a 30 degree angle to the shaft's longitudinal axis 15, whereas trailing surface 50 might be disposed at a 75 degree angle to the shaft's longitudinal axis 15. Preferably leading surface 45 and trailing surface 50 meet at a sharp point 55.

Surgical fastener 5 also comprises a bar 60 which projects radially outwardly from the fastener's top surface 20, adjacent to proximal end surface 35. Bar 60 is adapted to present the greatest possible resistance to tissue when the fastener is being passed, distal end first, through tissue. To this end, bar 60 extends generally radially outwardly from shaft 10, and comprises a distal surface 65 and a proximal surface 70. Preferably bar 60 leans slightly distally, in the manner shown in FIGS. 1 and 2, as will hereinafter be disclosed in further detail. By way of example, bar 60 preferably extends at a 75 degree angle to the shaft's longitudinal axis 15.

As seen in FIGS. 2 and 3, each fin 40 and the bar 60 is preferably sized so as to have a width slightly less than the width of shaft 10, for reasons which will hereinafter be disclosed in further detail. Furthermore, as seen in FIG. 1, it is preferred that the fastener's bar 60 sit higher above the fastener's top surface 20 than fins 40, for reasons which will hereinafter also be disclosed in further detail.

Surgical fastener 5 may be formed in a variety of different sizes, according to its intended use. By way of example, where surgical fastener 5 is to be used to close a tear in a piece of meniscal tissue, surgical fastener 5 might be formed with the following dimensions:

| | |
|---|---|
| total length | 10.0 mm |
| barb height | 2.0 mm |
| bar height | 2.5 mm |
| shaft width | 1.0 mm |
| barb width | 0.8 mm |
| bar width | 0.8 mm |

Surgical fastener 5 is formed out of a bio-compatible material, whereby it may be installed in living tissue without causing adverse reaction. By way of example, surgical fastener 5 may be formed out of a non-absorbable bio-compatible material of the sort well known in the art, e.g., acetal or polyethylene. Alternatively, surgical fastener 5 may be formed out of an absorbable bio-compatible material of the sort well known in the art, e.g., polylactic acid (PLA) or polyglycolic acid (PGA) or polycaprolactone (PCL) or trimethylene carbonate (TMC) or a blend, mix or copolymer of these or the like.

Surgical fastener 5 may be manufactured by any manufacturing process consistent with its composition. By way of example, but not limitation, where surgical fastener 5 is formed out of acetal or polyethylene, it may be molded in a mold or stamped and formed from a large sheet. Alternatively, where surgical fastener 5 is formed out of PLA or PGA or PCL or TMC or a blend, mix or copolymer of these or the like, they may be molded in a mold.

Looking next at FIGS. 4-6, there is shown an installation tool 75. Installation tool 75 comprises an inserter 80 extending along a longitudinal axis 85 and having a top surface 90 and a bottom surface 95. The distal end of inserter 80 comprises a carrier portion 83 which terminates in a sharp point 100. Preferably sharp point 100 is formed by sloping the inserter's distal end surface 101 (FIG. 4) at an angle of 30 degrees relative to longitudinal axis 85.

The inserter's carrier portion 83 is adapted to carry surgical fastener 5 for deployment of that fastener in tissue. More particularly, the inserter's carrier portion 83 comprises a recess 105 which is formed in the distal end of inserter 80, extending proximally from sharp point 100. Recess 105 provides a seat for surgical fastener 5 as will hereinafter be disclosed in further detail. To this end, recess 105 defines a floor 110 and terminates at a shoulder 115. Preferably recess 105 is created by forming a proximally-extending bore 120 (FIG. 6) in the distal end of inserter 80, and then cutting a slot 125 (FIG. 6) in the inserter's top surface 90. By forming slot 125 so that it has a width slightly less than the diameter of bore 120 (FIG. 6), recess 105 can be provided with a keyway-type configuration.

Looking next at FIGS. 7-9, surgical fastener 5 is intended to be seated in the installation tool's carrier portion 83 prior to deployment of the fastener into tissue. More particularly, surgical fastener 5 is intended to be backed into the installation tool's distal recess 105 so that the fastener's shaft 10 is received in the inserter's bore 120 and the fastener's fins 40 and bar 60 protrude out the top of inserter 80, through the inserter's slot 125. As seen in FIGS. 7 and 8, surgical fastener 5 and installation tool 75 are sized so that when the surgical fastener's proximal end surface 35 engages the installation tool's shoulder 115, the surgical fastener's distal end surface 30 will sit completely within the inserter's bore 120, withdrawn from the installation tool's sharp point 100. Furthermore, as seen in FIG. 9, surgical fastener 5 and installation tool 75 are sized so that only the fastener's fins 40 and bar 60, and not its shaft 10, will be able to protrude out through the shaft's top slot 125. This construction ensures that surgical fastener 5 can enter and exit the inserter's recess 105 only via the distal end of the recess, adjacent to the installation tool's sharp point 100. Surgical fastener 5 and installation tool 75 are also sized so that the surgical fastener will make a close sliding fit with the walls of the inserter's recess 105, whereby the fastener will be supported by the inserter, yet be able to move axially along recess 105.

A handle (not shown) is attached to the proximal end of inserter 80 by which the installation tool may be grasped by a user. By way of example, but not limitation, a screwdriver sort of handle, or a pistol grip sort of handle, might be attached to the proximal end of the inserter.

It will be appreciated that the dimensions of installation tool 75 are carefully coordinated with the dimensions of surgical fastener 5, and that these dimensions may vary according to the fastener's intended use. By way of example, where surgical fastener 5 has a total length of 10 mm, a barb height of 2 mm, a bar height of 2.5 mm, a shaft width of 1 mm, a barb width of 0.8 mm and a bar width of 0.8 mm, installation tool 75 might be formed with the following dimensions:

| | |
|---|---|
| inserter height | 1.5 mm |
| inserter width | 1.5 mm |
| recess length (to point 100) | 10.5 mm |
| slot width | 0.85 mm |
| bore diameter | 1.1 mm |

Surgical fastener 5 and installation tool 75 can be used to fasten one piece of tissue to another piece of tissue. By way of example, but not limitation, surgical fastener 5 and installation tool 75 can be used to close a tear in a piece of meniscal cartilage located within the interior of a knee joint.

More particularly, and looking now at FIG. 10, surgical fastener 5 and installation tool 75 can be used to close a tear 130 formed in a piece of meniscal cartilage 135 in the following manner.

First, surgical fastener 5 is loaded into installation tool 75 by backing the fastener into the installation tool's recess 105 so that the fastener sits in the inserter in the manner shown in FIGS. 7-9. In this arrangement, the only portions of surgical fastener 5 that protrude out of installation tool 75 are the upper portions of the fastener's fins 40 and bar 60.

Next, the distal end of installation tool 75 is positioned on the proximal side of tear 130, with the inserter's sharp point 100 adjacent to the outer surface of meniscal cartilage 135. Then the inserter's sharp point 100 is forced into the meniscal cartilage and across tear 130 (FIG. 11). As this occurs, surgical fastener 5 is carried through meniscal tissue 135 by inserter 80. It should be appreciated that surgical fastener 5 passes through the meniscal tissue without appreciable hindrance since the portions of fins 40 protruding from the inserter's recess 105 are configured to slide easily through the tissue in a distal direction. Forward movement of inserter 80 and surgical fastener 5 continues until the portion of the fastener bar 60 protruding from the inserter's recess 105 engages the outer surface of meniscal tissue 135. This engagement inhibits further movement of the assembly into the cartilage, since bar 60 is configured so as to inhibit movement through tissue in a distal direction. In this respect it should be appreciated that this is particularly true inasmuch as bar 60 is oriented with a slight distal lean, so as to increase the bar's resistance to distal movement through tissue. At this point the force of the fastener's bar 60, pressing against the outer surface of meniscal cartilage 135, will tend to close up tear 130 (FIG. 11).

Next, installation tool 75 is withdrawn from meniscal cartilage 135. As this occurs, the portions of the fastener's fins 40 protruding from the inserter's recess 105 catch on the meniscal cartilage disposed on the distal side of tear 130. This causes surgical fastener 5 to remain in place within meniscal cartilage 135 as the installation tool is withdrawn from the cartilage. Surgical fastener 5 sits within meniscal cartilage 135, with the meniscal cartilage on the distal side of tear 130 being prohibited from moving in a distal direction by the fastener's fins 40, and with the meniscal cartilage on the proximal side of tear 130 being prohibited from moving in a proximal direction by the fastener's bar 60. This effectively keeps tear 130 closed so as to facilitate healing of the meniscal cartilage (FIG. 12).

It is to be appreciated that surgical fastener 5 is preferably sized so as to ensure that the fastener's distal end surface 30 is completely buried within the receiving tissue. This will prevent the distal end of the surgical fastener from engaging, and possibly interfering with, any bodily structures which may lie on the far side of the receiving tissue. Thus, for the exemplary meniscal cartilage application discussed above, surgical fastener 5 would be sized so that its distal end surface 30 is buried within the meniscal cartilage 135 when the fastener's bar 60 bears against the outer surface of the meniscal cartilage. As a result, the distal end of the fastener will be insulated from engagement with any bodily structures which may lie on the far side of the cartilage.

However, in this respect it is also to be appreciated that, even if the distal end of surgical fastener 5 should inadvertently protrude from the far side of the cartilage, the deliberately rounded configuration of the fastener's distal end surface 30 will permit it to gently engage any such bodily structures, without any adverse consequences to such structures. This is an extremely important feature and a major advance over prior art fastening systems, which generally utilize surgical fasteners having sharply pointed distal end structures. Thus the present invention can be used safely in many situations (e.g., joint surgery) where prior art fasteners cannot be used safely. In this respect it is also to be appreciated that it is possible to provide surgical fastener 5 with its aforementioned rounded distal end surface 30 inasmuch as the present invention relies on the installation tool's sharp point 100, and not on the fastener's distal end surface 30, to open a way in the tissue.

Furthermore, inasmuch as it is the installation tool's sharp point 100 which opens a way in the tissue for the fastener, and not the surgical fastener's distal end surface 30, the fastener's shaft does not have to be made particularly rigid. Rather, some or all of the surgical fastener's shaft 10 can be made somewhat flexible, if desired, so long as the fastener's barbs 40 and bar 60 are given sufficient structural support to permit them to maintain their orientation vis-a-vis the receiving tissue. This is another extremely important feature and another significant advantage over prior art fastening systems, which generally require that a rigid shaft be provided to permit tissue penetration.

It is also to be appreciated that inasmuch as surgical fastener 5 is formed with a rounded proximal surface 35, and inasmuch as the fastener's bar 60 is configured so as to lean slightly in a distal direction, the proximal end of fastener 5 will present a non-obtrusive presence on the surface of meniscal cartilage 135. As a result, the proximal end of the fastener will not pose a threat to any bodily structures which may lie on the near side of the cartilage.

Since it is intended that surgical fastener 5 may be formed fairly small (e.g., a length of about 1 cm in the meniscal cartilage application), it is preferred that means be provided to facilitate handling of the fastener, both during manufacture of the fastener and during loading of the fastener into installation tool 75 or into some other installation tool formed in accordance with the present invention.

To this end, it is preferred that (i) a grip 140 (FIGS. 13 and 14) be provided in association with surgical fastener 5, whereby the fastener can be more easily manipulated during manufacture of the fastener, and (ii) a holder 145 (FIGS. 15 and 16) be provided for holding surgical fastener 5 and its associated grip 140 prior to loading the surgical fastener into its associated installation tool. In accordance with the present invention, a second installation tool 150 (FIGS. 17-19) is also disclosed for use in conjunction with surgical fastener 5, grip 140 and holder 145.

More particularly, and looking now at FIGS. 13 and 14, a surgical fastener 5 is shown attached to a grip 140 via a pair of tabs 155. Grip 140 essentially comprises a relatively large, generally rectangular mass or plate 160 which, due to its relative size, is more easily manipulated by hand than fastener 5. Thus, the provision of grip 140 will facilitate handling of fastener 5 during manufacture of the fastener. Tabs 155 extend between grip 140 and fastener 5. As seen in FIG. 14, tabs 155 have a reduced thickness adjacent to fastener 5, so as to facilitate separation of the fastener from the tabs, as will hereinafter be disclosed in further detail. It is preferred that fastener 5, grip 140 and tabs 155 all be formed at the same time, out of the same material, as part of a single complete assembly, e.g., by molding.

As noted above, the assembly shown in FIGS. 13 and 14 is preferably used in conjunction with the holder 145 shown in FIGS. 15 and 16. More particularly, it is envisioned that surgical fastener 5 and grip 140 will be packaged in holder 145 at the time of manufacture, and then removed from the holder at the time that the fastener is to be used in a surgical procedure. To this end, holder 145 includes a first recess 165 for accommodating shaft 10 of fastener 5, an adjacent opening 170 for accommodating fins 40 and bar 60 of surgical fastener 5, and an adjacent opening 175 for accommodating grip 140 associated with fastener 5. Holder 145 also comprises an opening 180 for permitting an installation tool to enter holder 145 and to engage, and then withdraw, the surgical fastener 5 from the holder, as will hereinafter be disclosed in further detail. To this end, opening 180 communicates with both opening 165 and opening 170. A shoulder 185 is formed at the point where openings 165, 170 and 180 meet. Preferably holder 145 is formed out of two mirror halves 145A and 145B (FIG. 16) so as to facilitate the manufacture of holder 145 and the positioning of surgical fastener 5 and grip 140 in the holder.

Figure 17:
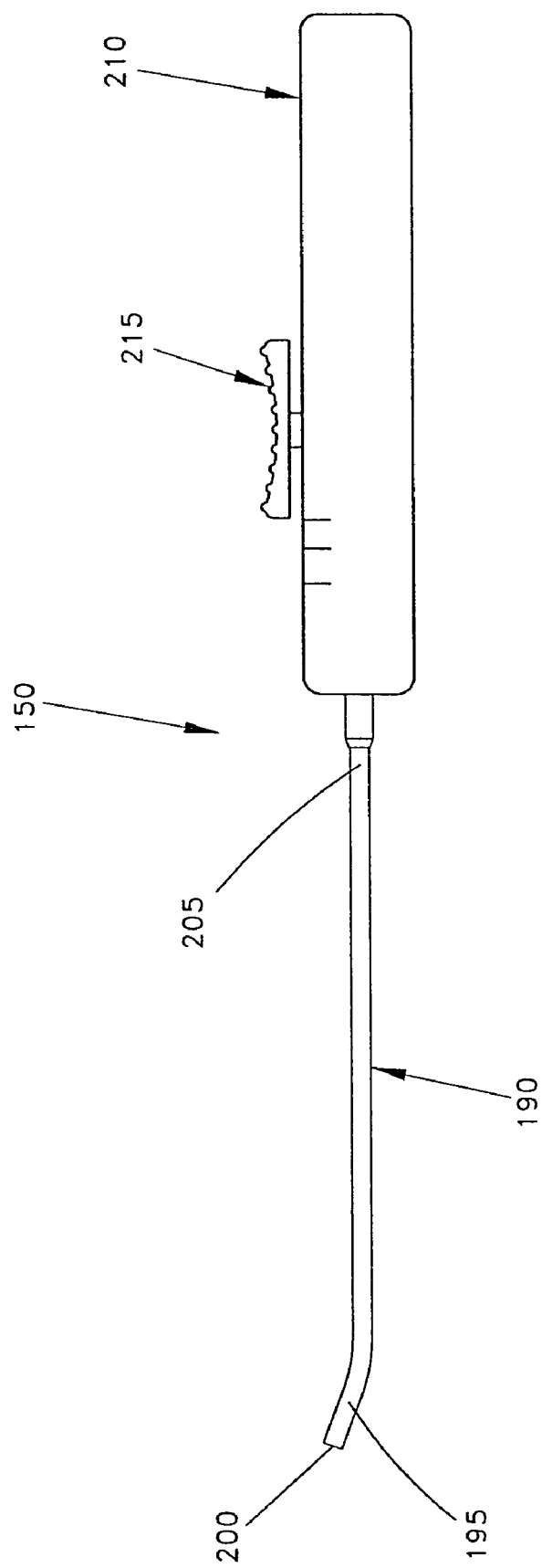
FIG. 17 is a side view of a second installation tool for deploying the surgical fastener of the present invention, with this installation tool being shown with its inserter positioned in a first, retracted position.
Figure 18:
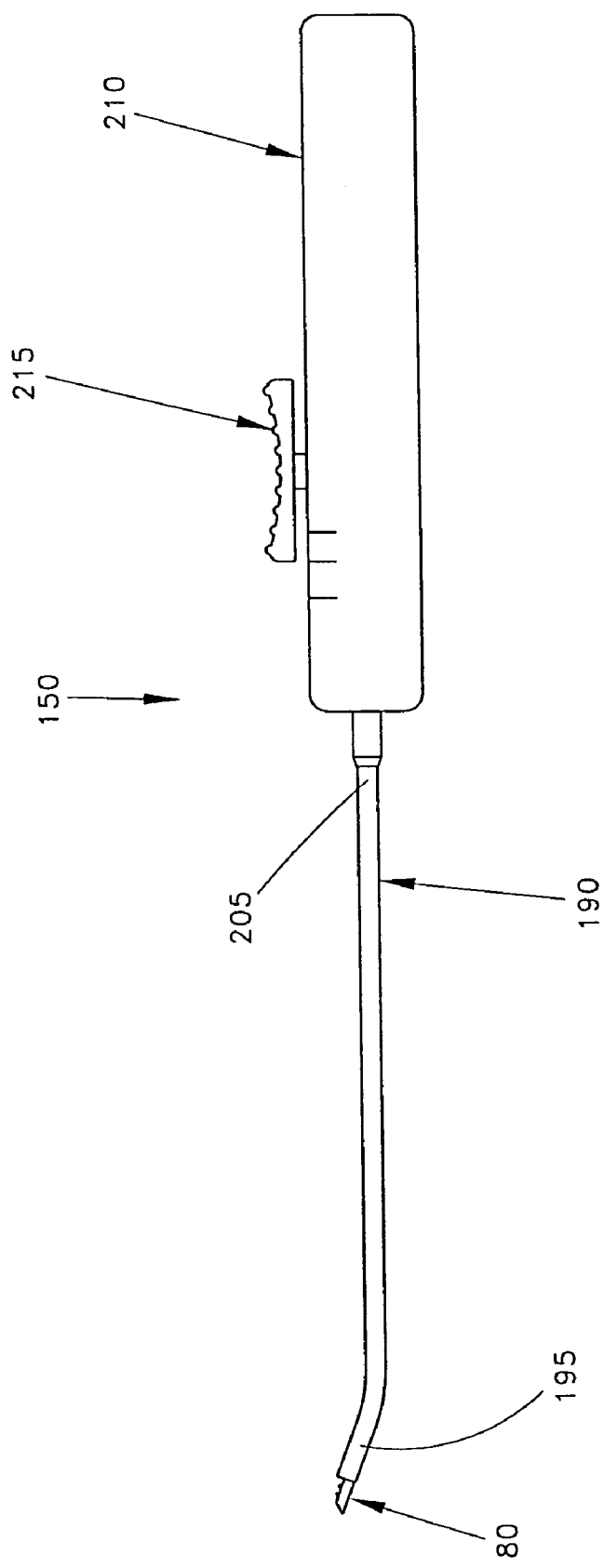
FIG. 18 is a side view of the second installation tool, but with the installation tool being shown with its inserter positioned in a second, partially-extended position.
Figure 19:
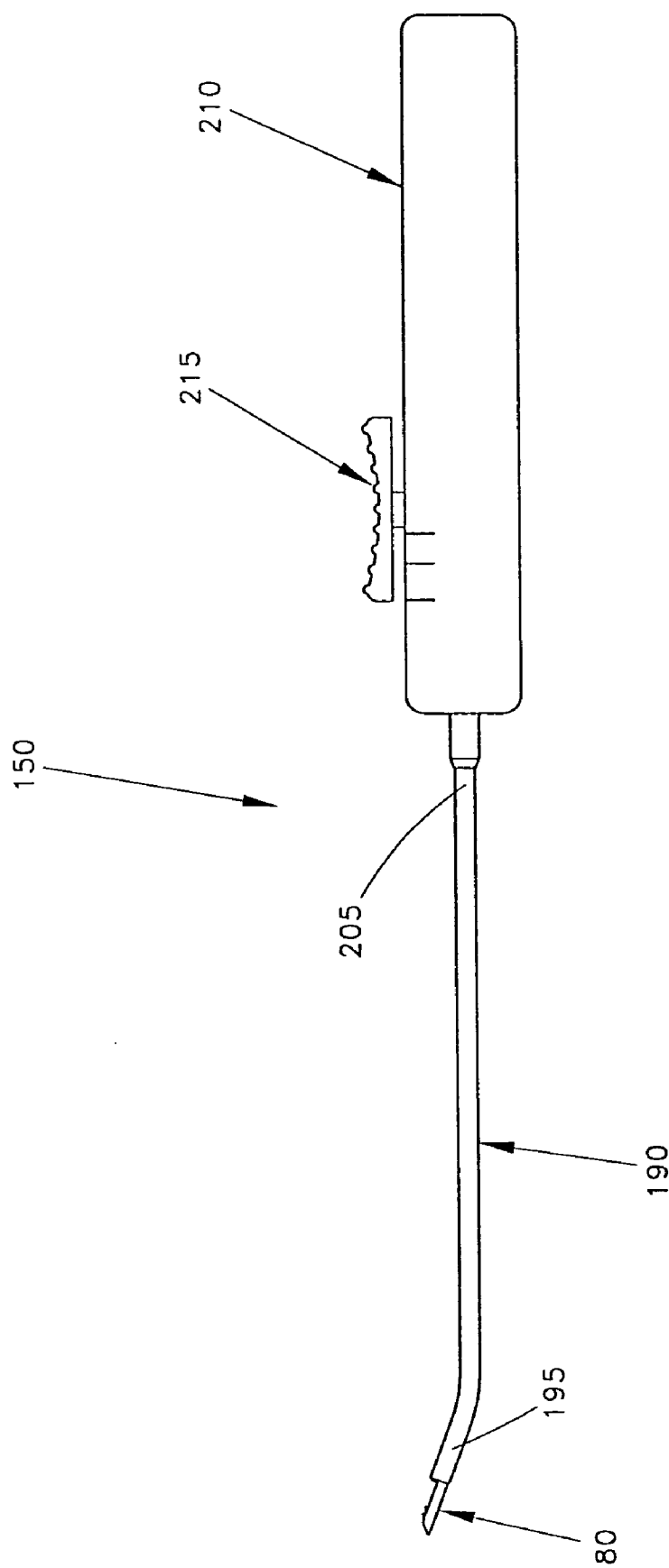
FIG. 19 is a side view of the second installation tool, but with the installation tool being shown with its inserter positioned in a third, fully-extended position.

Looking next at FIGS. 17-19, a second installation tool 150 is shown which may be used in conjunction with the present invention. Installation tool 150 comprises an inserter 80 (FIGS. 18 and 19) similar to the inserter 80 disclosed above. Inserter 80 is slidably disposed with an elongated tube 190. Tube 190 includes a distal end 195 terminating in a distal end surface 200, and a proximal end 205. Distal end surface 190 is preferably flat, whereby tube 190 will present a blunt distal end. The proximal end 205 of tube 190 is connected to a handle 210. Handle 210 includes a button 215 which is connected to the proximal end of inserter 80 via selected means of the sort well known in the art (not shown) whereby button 215 may be used to position inserter 80 in (i) a first retracted position, wherein the distal end of the inserter is withdrawn into the interior of tube 190 (FIG. 17), (ii) a second, partially-extended position, wherein the inserter's sharp point 100 and a portion of its recess 105 will be projected out of the distal end of the installation tool's tube 190 (FIG. 18), and (iii) a third, fully-extended position, wherein all of the inserter's recess 105 will be projected out of the distal end of the installation tool's tube 190 (FIG. 19). In addition to the foregoing, the installation tool's tube 190 is sized so that it can accommodate a surgical fastener 5 carried by inserter 80. By way of example, where surgical fastener 5 and inserter 80 have the exemplary dimensions recited previously, tube 190 might have the following dimensions:

| | |
|---|---|
| tube inner diameter height | 3.2 mm |
| tube inner diameter width | 1.8 mm |
| tube outer diameter height | 3.7 mm |
| tube outer diameter width | 2.3 mm |

Thus it will be appreciated that when the installation tool's inserter 80 is in (i) its first, retracted position (FIG. 17), a surgical fastener 5 carried by the inserter's carrier portion 83 will be disposed completely within tube 190, (ii) its second, partially-extended position (FIG. 18), a surgical fastener 5 carried by the inserter's carrier portion 83 will have its fins 40 exposed out the distal end of tube 190 but its bar 60 shielded within tube 190, and (iii) its third, fully-extended position (FIG. 19), a surgical fastener 5 carried by the inserter's carrier portion 83 will have its fins 40 and bar 60 exposed out the distal end of tube 190.

As seen in FIGS. 17-19, tube 190 is preferably bent slightly near its distal end 195, so as to facilitate deployment of surgical fastener 5. To this end, inserter 80 is formed so as to have sufficient flexibility to permit it to move easily through this bend as the inserter is moved between its aforementioned first, second and third position (i.e., the positions shown in FIGS. 17, 18 and 19, respectively). At the same time, however, inserter 80 is formed so as to have sufficient structural integrity to permit it to penetrate the receiving tissue, so as to deploy the surgical fastener in that tissue.

As noted above, the surgical fastener and grip assembly shown in FIGS. 13 and 14 is intended to be positioned within holder 145 at the time of manufacture, and then the surgical fastener loaded into second installation tool 150 at the time that the fastener is to be used in a surgical procedure.

Figure 20:
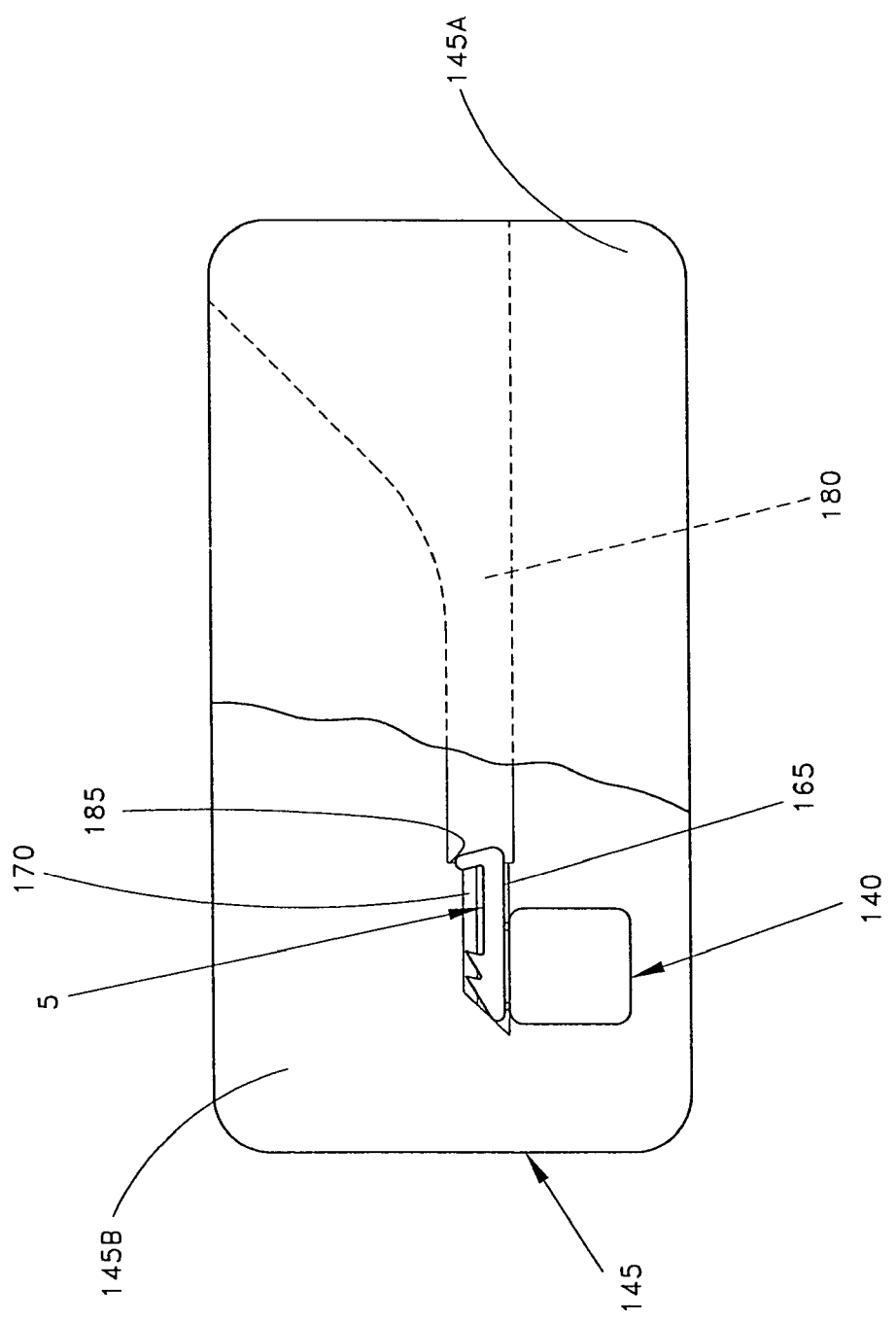
FIG. 20 is a side view showing the surgical fastener and grip of FIGS. 13 and 14 mounted in the holder of FIGS. 15 and 16, with selected portions of the holder being shown broken away.

More particularly, and looking next at FIG. 20, surgical fastener 5 and its associated grip 140 are intended to be positioned within holder 145 at the time of manufacture so that the fastener's shaft 10 is disposed in holder opening 165, the fastener's fins 40 and bar 60 are disposed in holder opening 170, and grip 140 is disposed in holder opening 175. As seen in FIG. 20, holder 145 is sized so that the proximal end of fastener 5 protrudes slightly beyond the holder's shoulder 185 and into holder opening 180.

Figure 21:
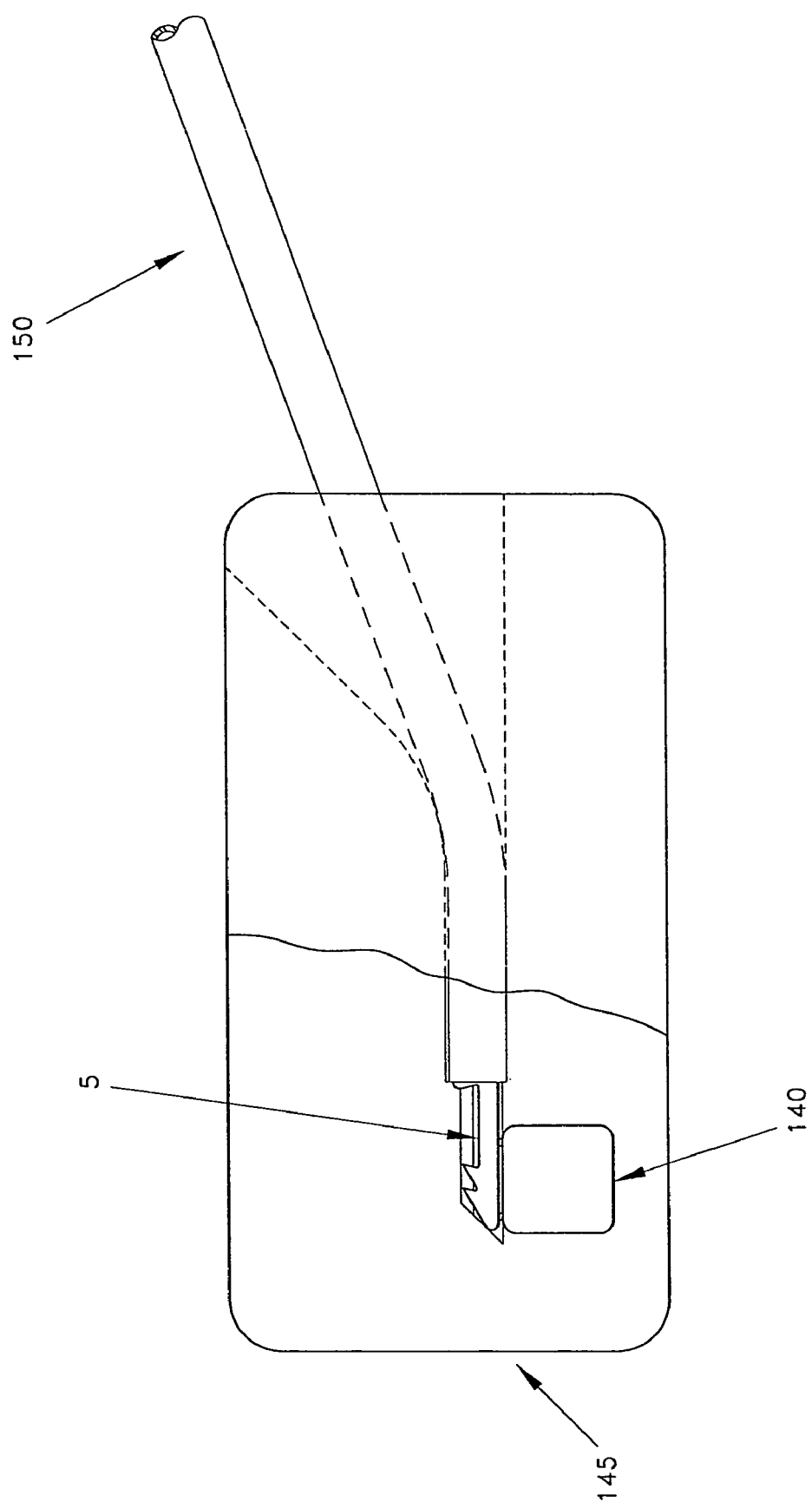
FIG. 21 is a side view of the same assembly as that shown in FIG. 20, except that the distal end of the second installation tool of FIGS. 17-19 is shown positioned adjacent to the proximal end of the surgical fastener, with the installation tool's inserter being positioned in its first, retracted position in preparation for loading the surgical fastener onto the inserter.

Looking next at FIG. 21, surgical fastener 5 is intended to be loaded into second installation tool 150 at the time that the fastener is to be used in a surgical procedure. More particularly, surgical fastener 5 is loaded into second installation tool 150 in the following manner.

First, installation tool 150 has its inserter 80 positioned in its first, retracted position (FIG. 17). Then the distal end 195 of the installation tool is inserted into holder opening 180 until the tube's distal end surface 200 engages holder shoulder 185. At this point recess 105 of the installation tool's inserter will be aligned with surgical fastener 5.

Figure 22:
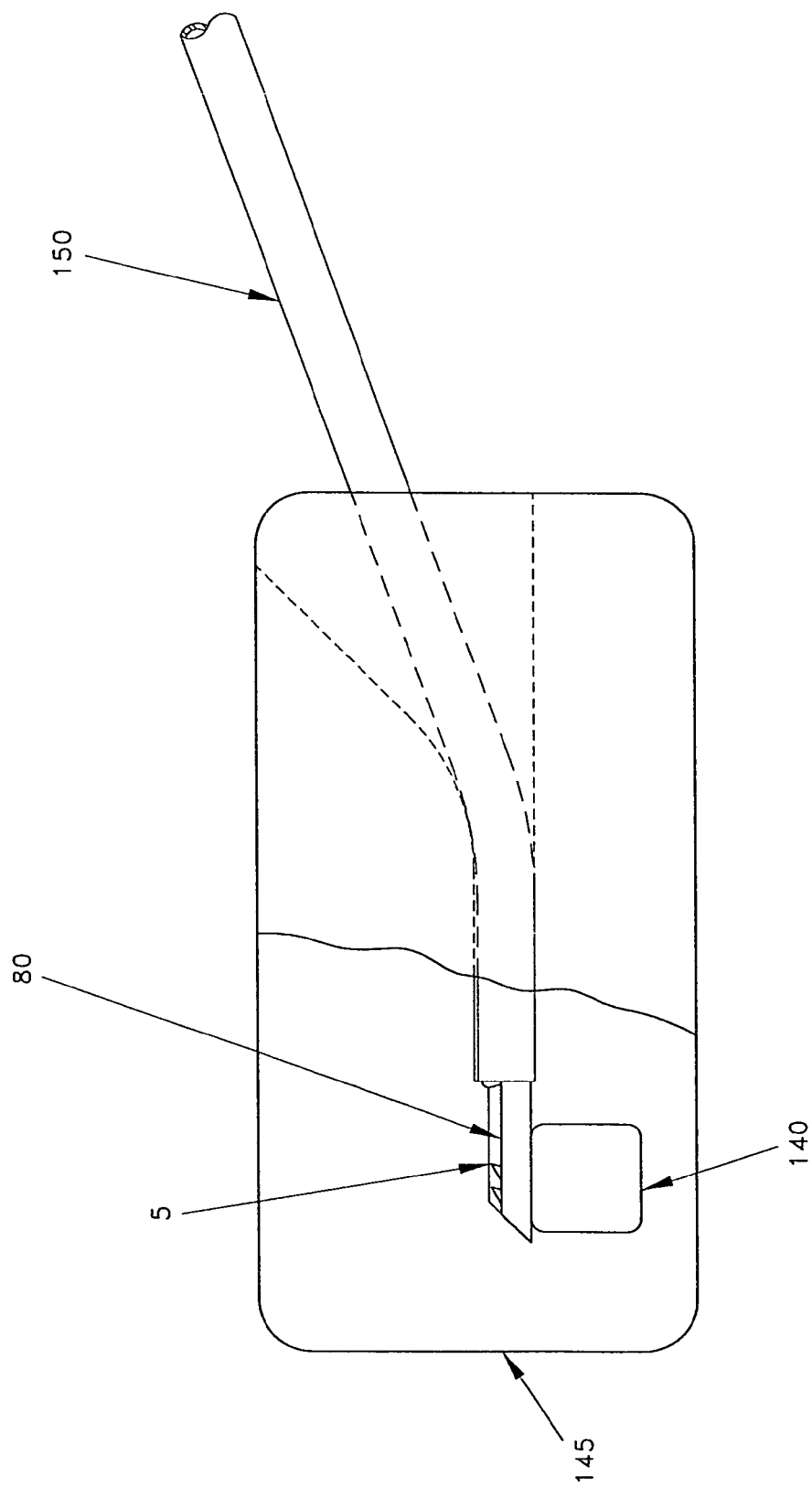
FIG. 22 is a side view of the same assembly as that shown in FIG. 21, except that the installation tool has had its inserter advanced from its first, retracted position to its third, fully-extended position so as to load the surgical fastener onto the inserter.
Figure 23:
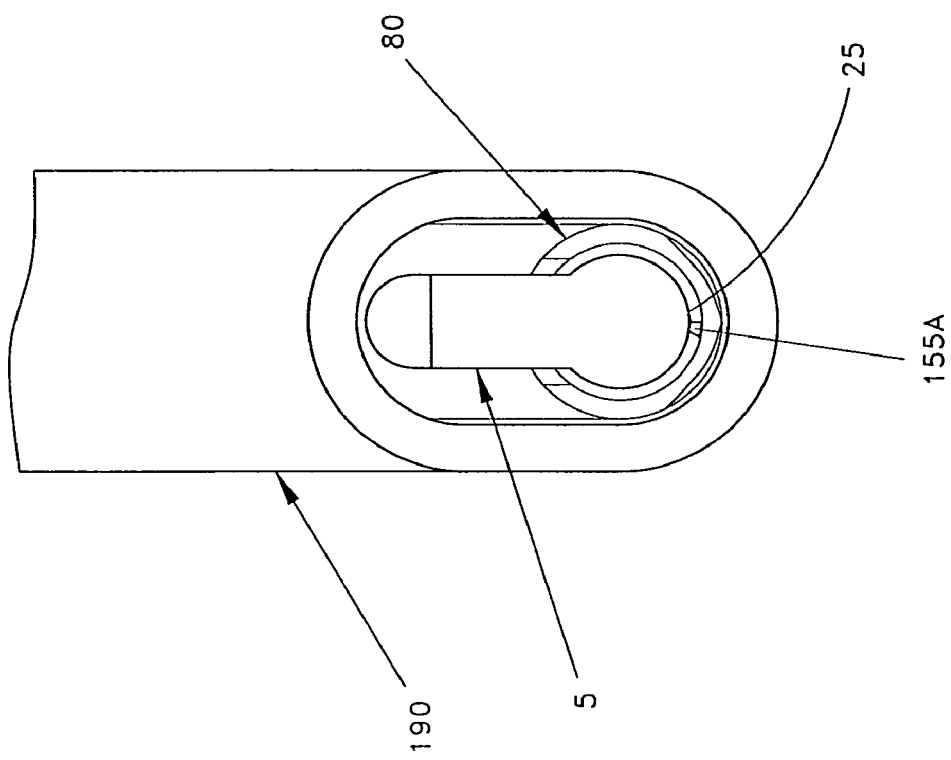
FIG. 23 is a front end view showing the surgical fastener loaded onto the second installation tool's inserter.

Next, the installation tool's inserter 80 is advanced from its first, retracted position to its third, fully-extended position (FIG. 22). As this occurs, the inserter's sharp point 100 will sequentially engage and then sever each of the tabs 155 holding surgical fastener 5 to grip 140, so as to free surgical fastener 5 from grip 140. At the same time that this occurs, the advancing inserter 80 will also envelope fastener 5 so that the fastener will be loaded into the inserter's recess 105. It is to be appreciated that, as the inserter severs tabs 155 and picks up fastener 5 in recess 105, small nibs 155A (FIG. 23) of tabs 155 remain attached to the fastener's bottom surface 25. These small nibs 155A give fastener 5 a slight upward bias within recess 105 of inserter 80, so as to cause fastener 5 to make a snug fit within that recess.

Figure 24:
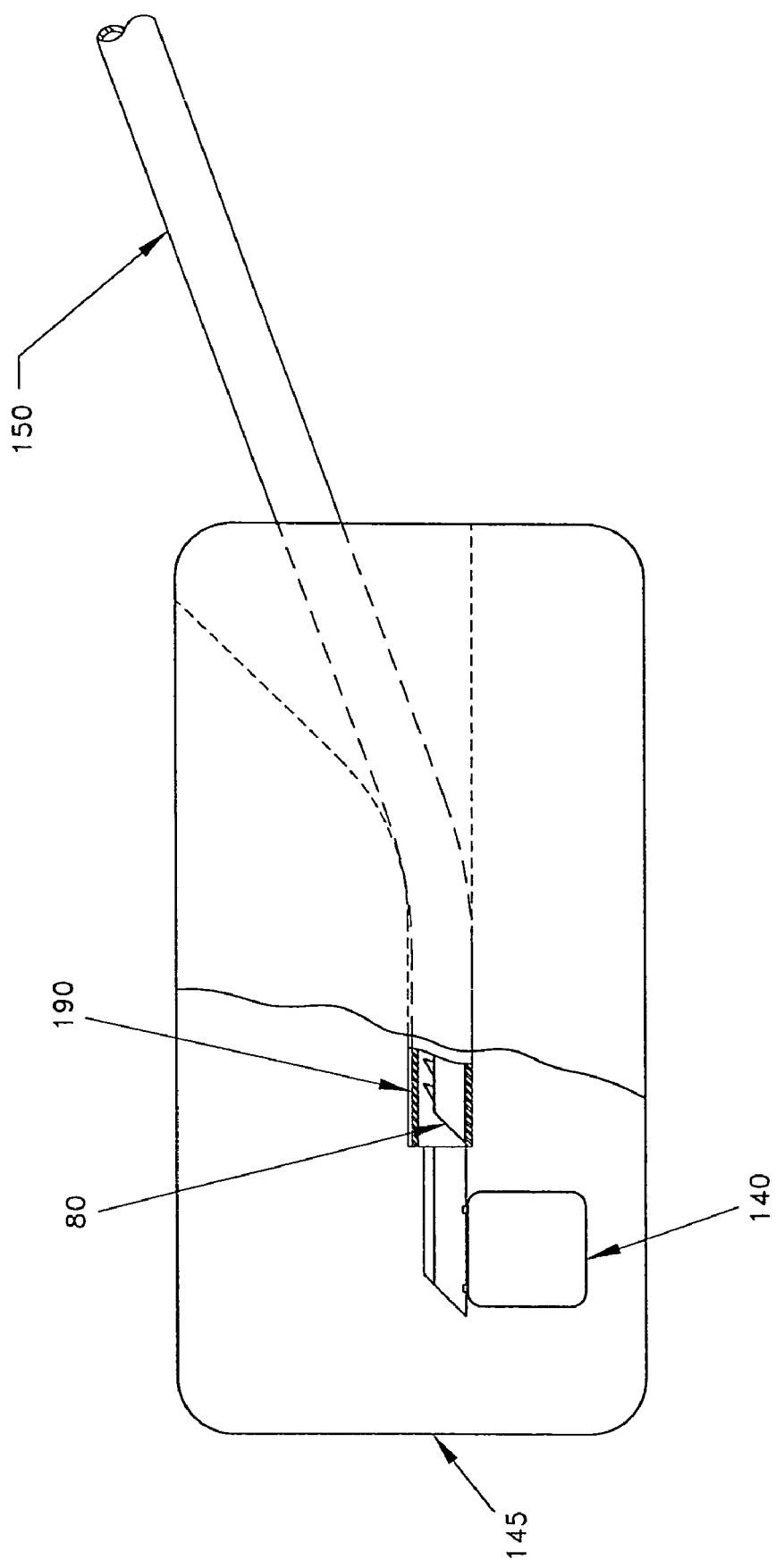
FIG. 24 is a side view of the same assembly as that shown in FIG. 22, except that the installation tool has had its inserter retracted from its third, fully-extended position to its first, retracted position so as to carry the surgical fastener back into the interior of the installation tool.

Next, inserter 80 is withdrawn back into tube 190 (FIG. 24). As this occurs, surgical fastener 5 is carried away from grip 140, and into tube 190, by the retreating inserter 80. Finally, installation tool 150 is withdrawn from holder 145. At this point, surgical fastener 5 will be loaded in the installation tool's inserter 80, ready to be deployed into tissue.

Once surgical fastener 5 has been loaded into second installation tool 150, the surgical fastener and the installation tool can be used to fasten one piece of tissue to another piece of tissue. By way of example, but not limitation, surgical fastener 5 and installation tool 150 can be used to close a tear in a piece of meniscal cartilage.

Figure 25:
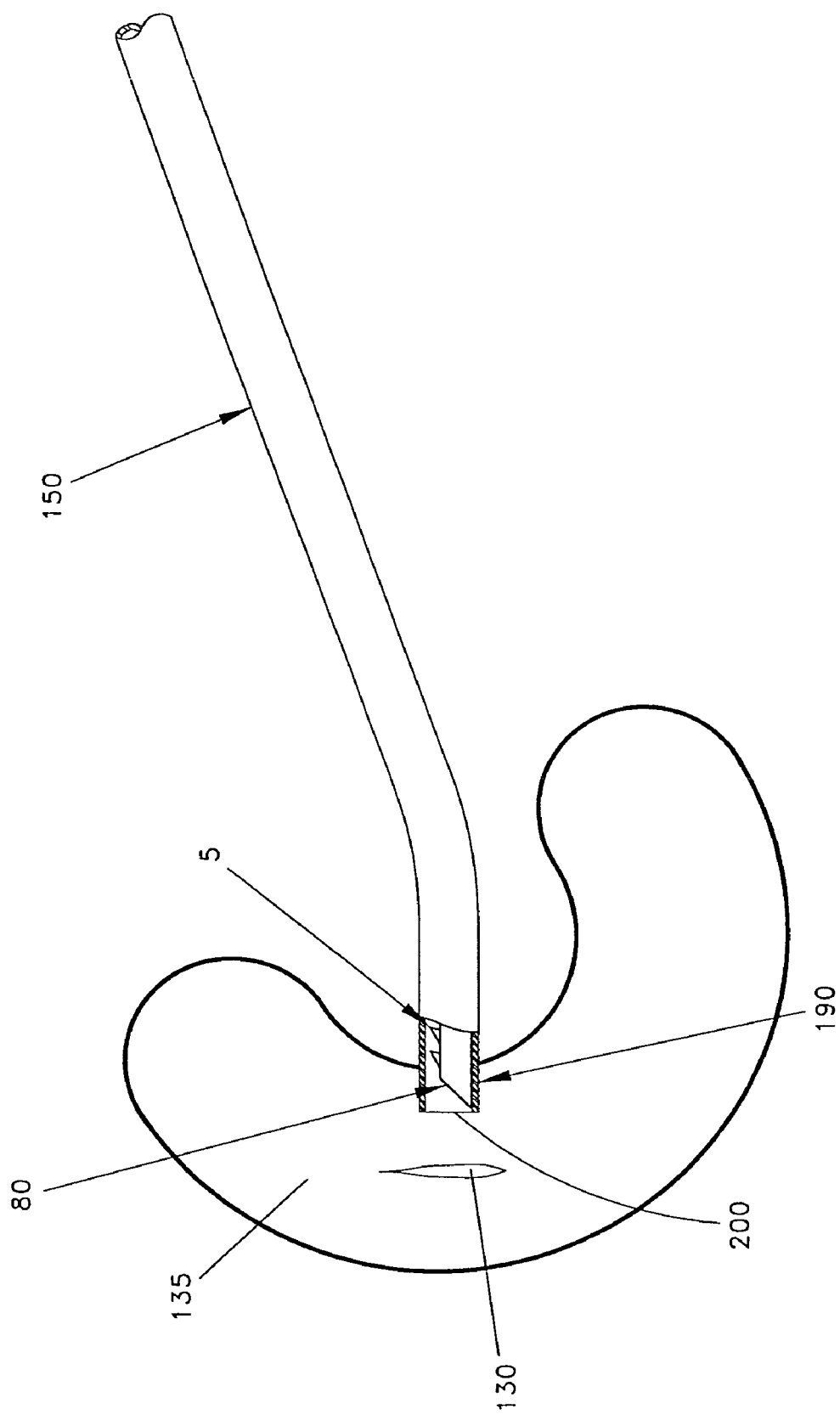
FIG. 25 is a side view showing the second installation tool, carrying the surgical fastener, approaching a tear located in a piece of meniscal cartilage, with the installation tool's inserter being positioned in its first, retracted position so that the surgical fastener is fully withdrawn into the interior of the installation tool.

More particularly, and looking now at FIG. 25, surgical fastener 5 and second installation tool 150 can be used to close a tear 130 formed in a piece of meniscal cartilage 135. This may be accomplished in the following manner.

First, the distal end of installation tool 150 is positioned on the proximal side of tear 130, with the tube's distal end surface 200 adjacent to the outer surface of the piece of meniscal cartilage 135 (FIG. 25). At this point, the installation tool's inserter 80 will be in its first, retracted position, so that fastener 5 will be completely encased in the installation tool's tube 190.

Figure 26:
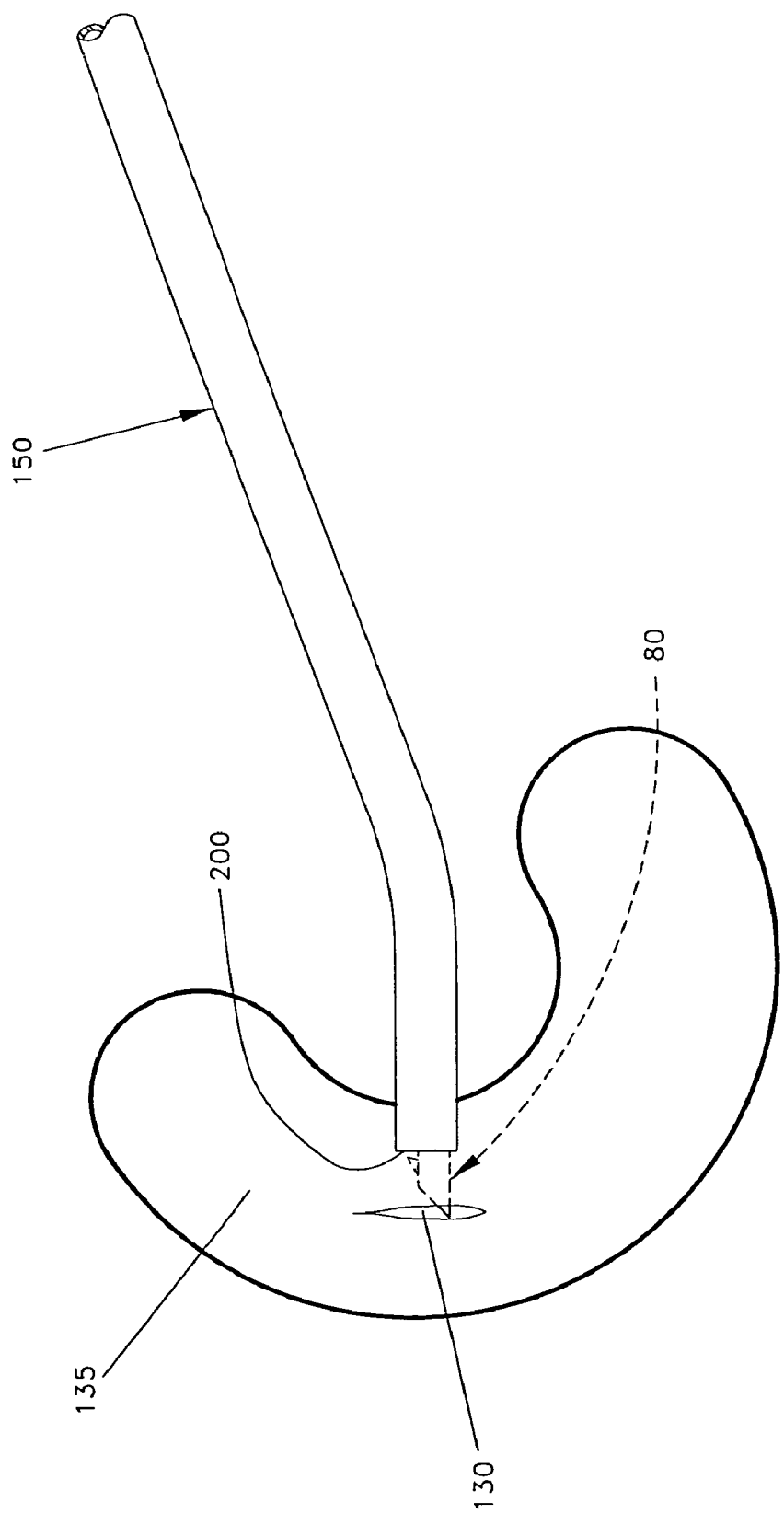
FIG. 26 is a side view like that of FIG. 25, except that the installation tool's inserter has been advanced into its second, partially-extended position as the surgical fastener is inserted into the piece of meniscal cartilage at the near side of the tear.

Next, the installation tool has its inserter 80 advanced into its second, partially-extended position, and the inserter's sharp point 100 is forced into the meniscal cartilage and across tear 130 (FIG. 26). As this occurs, surgical fastener 5 is carried through meniscal tissue 135 by inserter 80. As noted previously with respect to installation tool 75, inserter 80 is able to pass into the meniscal cartilage without significant impedance, since the portions of the fastener's fins 40 protruding from the inserter's recess 105 are configured to slide easily through the tissue in a distal direction. Forward movement of inserter 80 continues until the tube's distal end surface 200 engages the outer surface of meniscal tissue 135.

Figure 27:
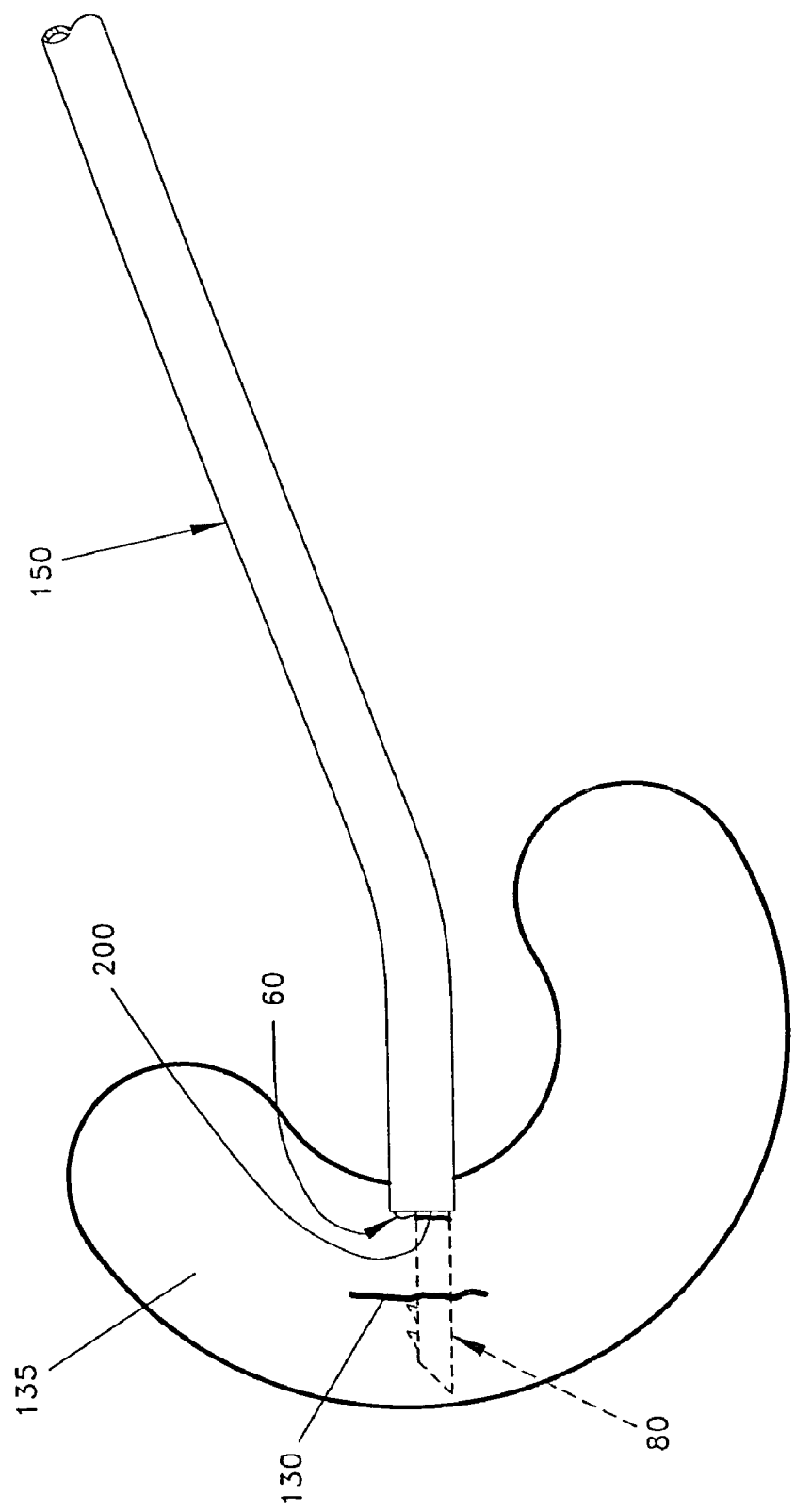
FIG. 27 is a side view like that of FIG. 26, except that the installation tool's inserter has been advanced into its third, fully-extended position as the surgical fastener is extended across the tear.

Next, the installation tool's inserter 80 is advanced from its second, partially-extended position to its third, fully-extended position. As this occurs, the installation tool's distal end surface 200 is kept pressed against the outer surface of the meniscal cartilage, compressing the tissue and thereby closing tear 130. Accordingly, the installation tool's inserter passes further into the tissue, until the fastener's bar 60 engages the outer surface of the meniscal cartilage (FIG. 27). At this point, further movement of the assembly into the cartilage is prohibited, since bar 60 is configured so as to prohibit movement through tissue in a distal direction.

Figure 28:
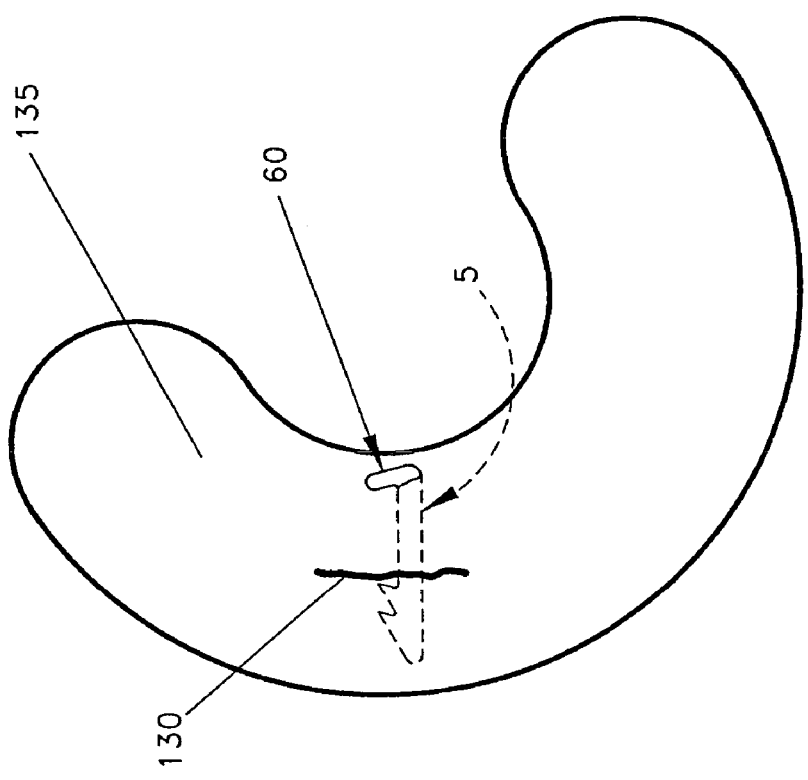
FIG. 28 is a side view showing the surgical fastener holding the aforementioned tear closed, with the installation tool having been removed from the surgical site.

Next, the installation tool's inserter 80 is moved from its third, fully-extended position (FIG. 27) to its first, fully retracted position. This causes the inserter to be withdrawn from meniscal cartilage 135. As this occurs, the portions of the fastener's fins 40 protruding from the inserter's recess 105 catch on the meniscal cartilage disposed on the distal side of tear 130. This causes fastener 5 to remain in place within meniscal cartilage 135 as the inserter is retracted back into the installation tool's tube 190. At the same time, the installation tool's distal end surface 200 is kept pressed tightly against the near surface of the cartilage, whereby tear 130 in meniscal cartilage 135 is kept closed as the retreating inserter 80 is withdrawn from the cartilage. Fastener 5 remains in meniscal cartilage 135, with the meniscal cartilage on the distal side of tear 130 being prohibited from moving in a distal direction by the fastener's fins 40, and the meniscal cartilage on the proximal side of tear 130 being prohibited from moving in a proximal direction by the fastener's bar 60. This effectively keeps tear 130 closed so as to facilitate healing of the meniscal cartilage (FIG. 28). Installation tool 150, which has its sharp inserter 80 safely sheathed within its tube 190, may then be withdrawn from the surgical site.

Figure 29:
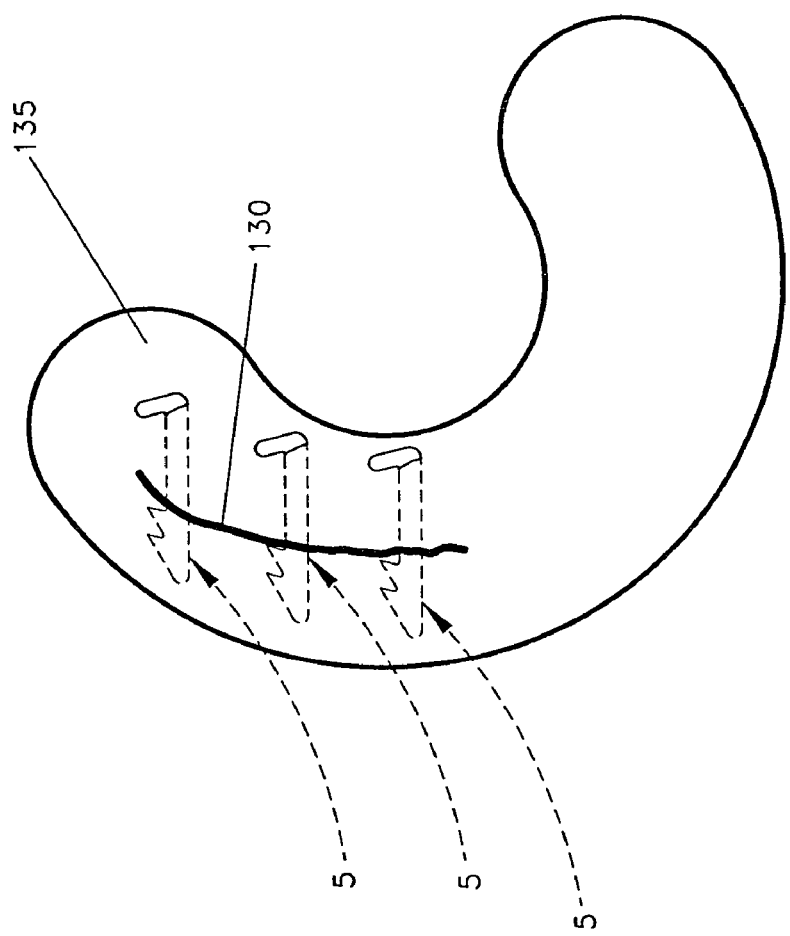
FIG. 29 is a side view like that of FIG. 28, except showing three surgical fasteners closing a tear in a piece of meniscal cartilage.

It is anticipated that some situations (e.g., the situation shown in FIGS. 12 and 28), a single fastener 5 may be sufficient to effect the desired tissue attachment. However, it is also anticipated that in other situations (e.g., the situation shown in FIG. 29) multiple fasteners may be used to effect the desired tissue attachment.

It is to be appreciated that the particular construction of installation tool 150 permits the installation tool to be moved to the surgical site while its sharp inserter 80 is safely sheathed within blunt tube 190, and thereafter removed from the surgical site while its sharp inserter 80 is safely sheathed within blunt tube 190. This is an important feature, particularly where the installation tool must be maneuvered around delicate bodily structures on its way to, and away from, the surgical site.

As disclosed above, surgical fastener 5 can be used to attach one piece of tissue to another piece of tissue. This was illustrated above in connection with closing a tear 130 in a piece of meniscal cartilage 135. However, it should also be appreciated that surgical fastener 5 can be used to effect many other types of tissue attachment. By way of further illustration, but not limitation, surgical fastener 5 might be used to repair a tear in a rotator cuff. Or surgical fastener 5 might be used to attach together other types of tissue, e.g., surgical fastener 5 might be used to attach skin to an underlying tissue structure, or it might be used in other types of plastic surgery, or it might be used to attach vascular tissue to an adjacent tissue structure, or it might be used to attach ocular tissue to an adjacent tissue structure. It is also possible to use surgical fastener 5 to attach a piece of "seed" tissue to an underlying tissue structure, where that "seed" tissue will be used to grow a predetermined body part onto that underlying tissue structure.

It is also to be appreciated that surgical fastener 5 can be used to attach bio-compatible inanimate objects to tissue. By way of example, surgical fastener 5 might be used to attach an inanimate device to soft tissue. In such a case, the inanimate device can be either absorbable or non-absorbable. By way of further example, surgical fastener 5 might be used to attach a woven material, or a filament, or a film-like material to tissue.

Conversely, it is also possible to use surgical fastener 5 to attach tissue to a bio-compatible inanimate object. For example, surgical fastener 5 might be used to attach a piece of tissue to a bio-compatible substrate, and then that substrate might in turn be attached to another piece of tissue.

Still other variations of this sort will be obvious to a person skilled in the art.

As noted above, the dimensions of surgical fastener 5 will vary according to its particular use.

Modifications of the Preferred Embodiments

It is, of course, possible to modify the preferred embodiments disclosed above without departing from the scope of the present invention.

Figure 30:
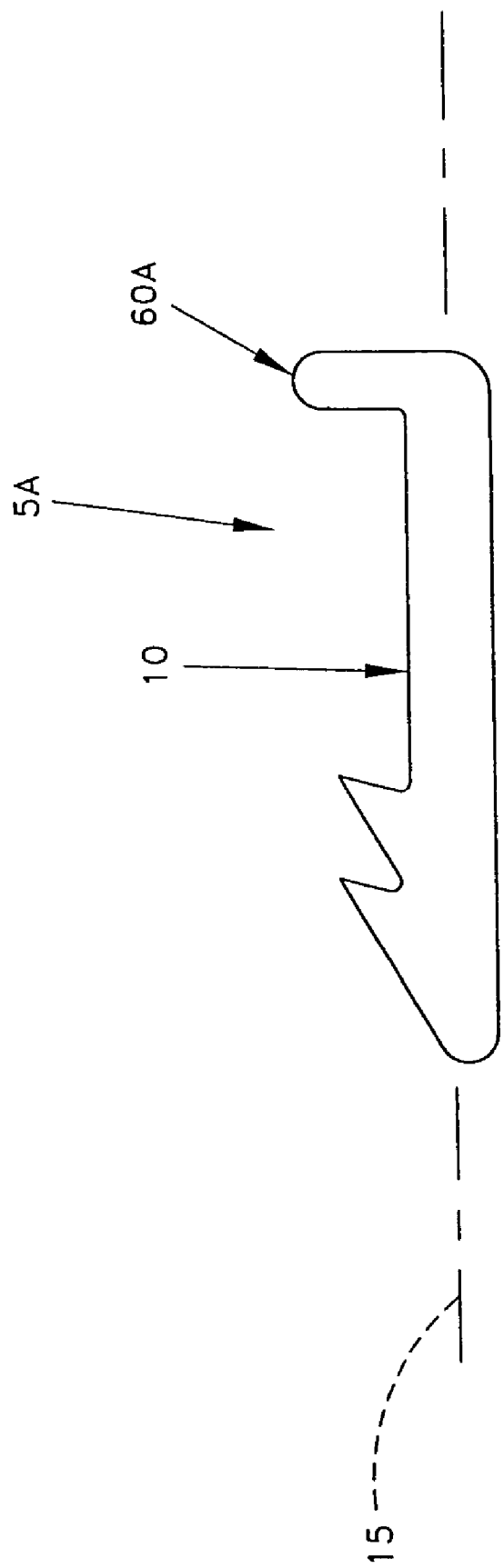
FIG. 30 is a side view of a second surgical fastener formed in accordance with the present invention.

Thus, for example, it is possible to provide a surgical fastener 5A such as that shown in FIG. 30. Surgical fastener 5A is identical to the surgical fastener 5 disclosed above, except that it has its bar 60A set at a substantially right angle to the axis 15 of its shaft 10.

Figure 31:
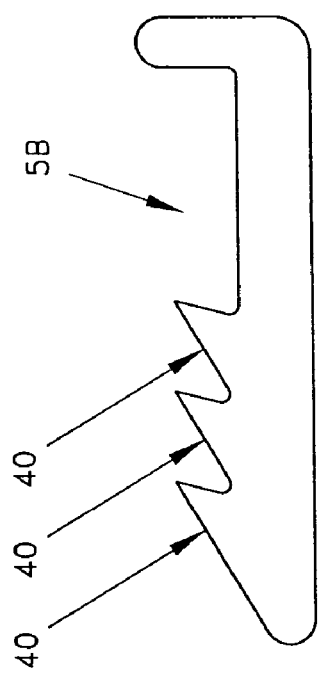
FIG. 31 is a side view of a third surgical fastener formed in accordance with the present invention.

It is also anticipated that one might provide a surgical fastener 5B such as that shown in FIG. 31. Surgical fastener 5B is identical to the surgical fastener 5A disclosed above, except that three fins 40 are provided at the distal tip of the fastener. Alternatively, more than three fins might be provided at the distal tip of the fastener.

Figure 32:
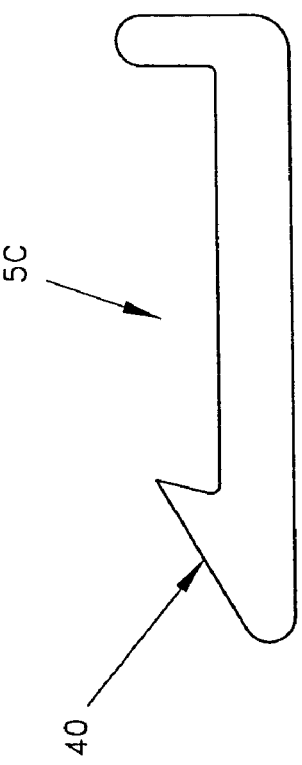
FIG. 32 is a side view of a fourth surgical fastener formed in accordance with the present invention.

It is also possible to provide a surgical fastener 5C such as that shown in FIG. 32. Surgical fastener 5C is identical to the surgical fastener 5A disclosed above, except that only one fin 40 is provided at the distal tip of the fastener.

Of course, fins 40 may have other shapes and/or sizes so as to be appropriate for particular tissue attachment procedures.

It is also anticipated that one might provide a surgical fastener 5D such as that shown in FIG. 33. Surgical fastener 5D is identical to the surgical fastener 5B disclosed above, except that the fastener's bar 60D includes a distally projecting portion 60D' which extends parallel to the fastener's shaft 10. Thus, fastener 5D is essentially provided with a hook-shaped rear end, where that hook is formed by the proximal end of shaft 10, bar 60D, and return 60D'.

It is, of course, possible to provide the fasteners 5A and 5C with similar hook-shaped rear ends. Thus, for example, a fastener 5E is shown in FIG. 34, where fastener 5E is identical to fastener 5C shown in FIG. 32, except that fastener 5E includes a hook-shaped rear end of the sort disclosed above, i.e., a hook formed by the proximal portion of shaft 10, bar 60E and return 60E'.

Figure 36:
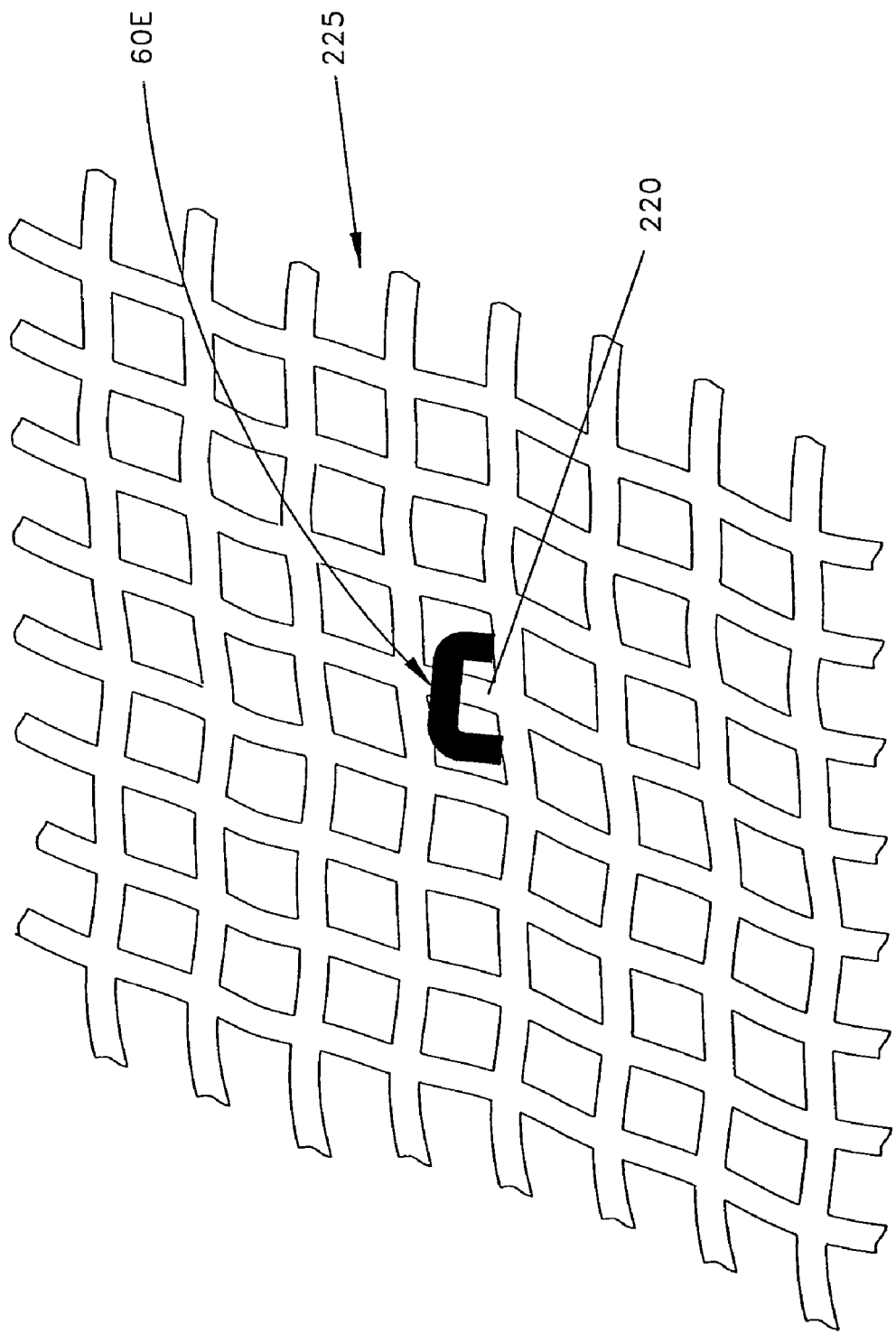
FIG. 36 is a perspective view showing the surgical fastener of FIG. 34 attaching the piece of surgical mesh to the piece of tissue.

By providing a hook-shaped rear end on the surgical fastener, it is possible to attach objects to tissue using the fastener's hook-shaped rear end. By way of example, but not limitation, it is possible to use a fastener such as the fastener 5E to attach a piece of surgical mesh to tissue, e.g., to abdominal tissue. More particularly, and looking now at FIGS. 35 and 36, in this situation a surgical fastener 5E is set so that its hook-shaped rear end captures a filament 220 of the surgical mesh 225 to tissue 230, with the filament being captured by the hook formed by the proximal end of fastener shaft 10, bar 60E and return 60E'.

Surgical fastener 5E might also be used to attach other objects to tissue, e.g., to capture a single long strand or filament to tissue.

Figure 38:
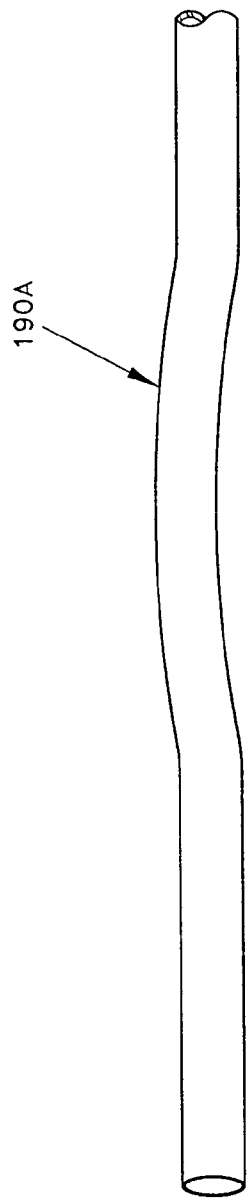
FIG. 38 is a side view showing the distal end of the third installation tool, with the third installation tool having been rotated 90 degrees from the position shown in FIG. 37.
Figure 37:
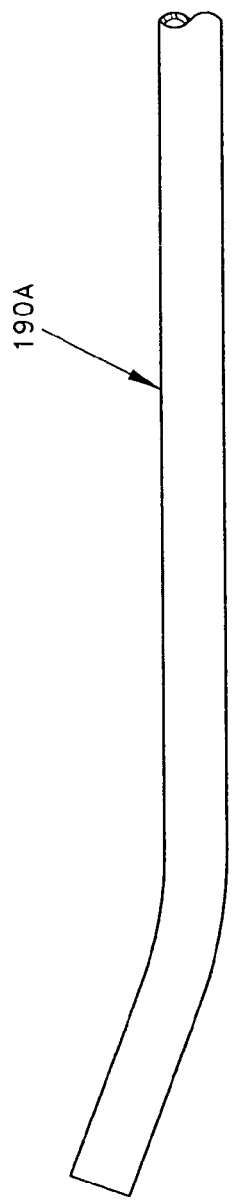
FIG. 37 is a partial side view showing the distal end of a third installation tool formed in accordance with the present invention.

It is also anticipated that, in certain circumstances, installation tool 75 or second installation tool 150 might be provided with a particular geometry to facilitate applying the fastener in hard-to-reach places. By way of example, in FIGS. 4-12, installation tool 5 is shown to have a substantially straight distal end; and in FIGS. 17-19 and 21-27, second installation tool 150 is shown to have a simple curve at its distal end. However, certain situations may call for a more complex shaft geometry to permit the distal end of the installation tool to reach a particular location. For example, and looking now at FIGS. 37 and 38, it is anticipated that one might form the second installation tool 150 so that it has an elongated tube 190A which includes compound curves. Such compound curves can prove exceedingly useful in navigating around various anatomical structures found within the body, e.g., in navigating around the condyles when closing a tear in a piece of meniscal cartilage within the knee joint.

It is also possible to form a staple-type of fastener out of two or more surgical fasteners of the sort disclosed above. Thus, for example, and looking now at FIGS. 39 and 40, a staple-type surgical fastener 240 can be formed out of two fasteners 5C of the sort disclosed above. In this situation, a bridge section 60C" extends between the two bars 60C so as to link the two fasteners 5C together. A modified installation tool 245, formed out of two installation tools 75 connected together in ways well known in the art (not shown), is used to insert the staple-type surgical fastener 240.

Figure 41:
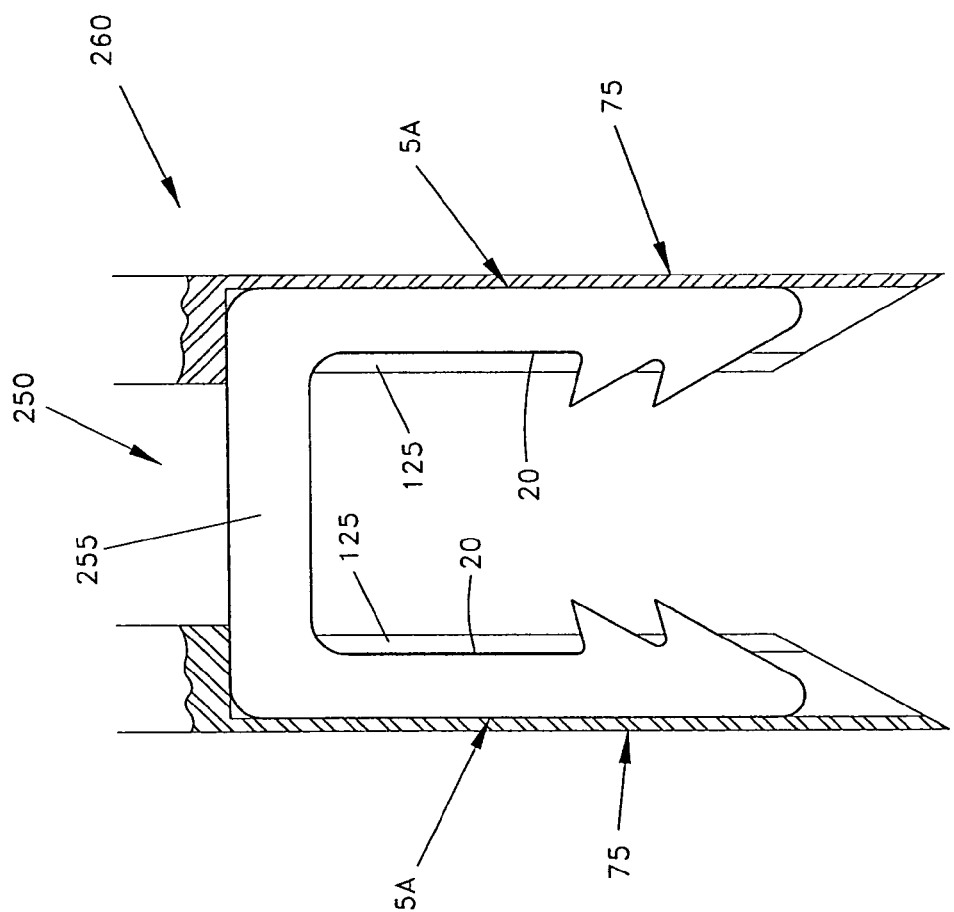
FIG. 41 is a partial top view, partially in section, of an assembly comprising an eighth surgical fastener formed in accordance with the present invention and an installation tool for deploying the same.

Yet another possible variation is shown in FIG. 41. Here two surgical fasteners 5A are combined so as to form a staple-type fastener 250. This is done by turning each of the surgical fasteners on its side so that their surfaces 20 face each other, extending the bar of each fastener, and then joining the two bars together so as to form a bridge 255. In this situation, the staple-type fastener 250 can be set by a modified installation tool 260. Installation tool 260 comprises two installation tools 75 of the sort described above, wherein the installation tools are turned on their sides so that their slots 125 face one another, and then connected together in ways well known in the art (not shown).

Figure 42:
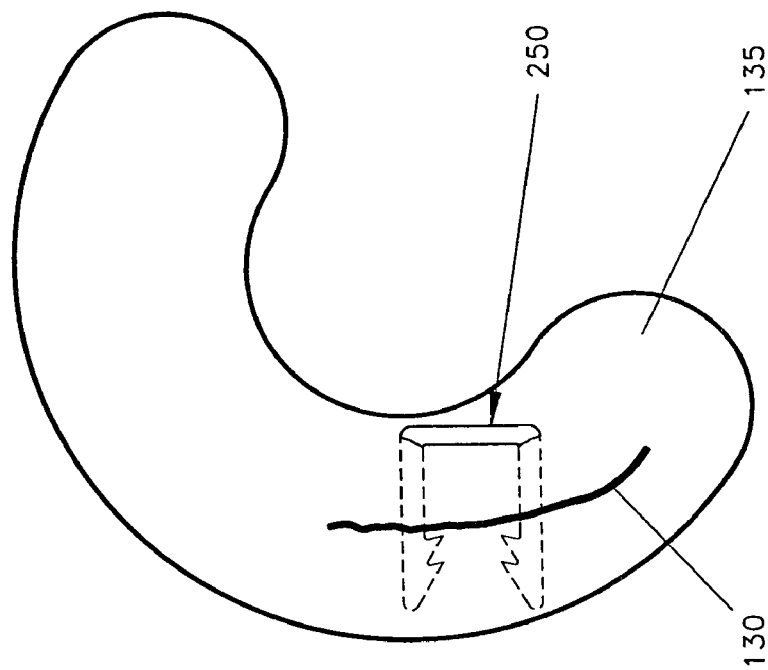
FIG. 42 is a side view showing the eighth surgical fastener of FIG. 41 closing a tear in a piece of meniscal cartilage.

FIG. 42 shows the staple-like fastener 250 closing a tear 130 in a piece of meniscal cartilage 135.

Figure 43:
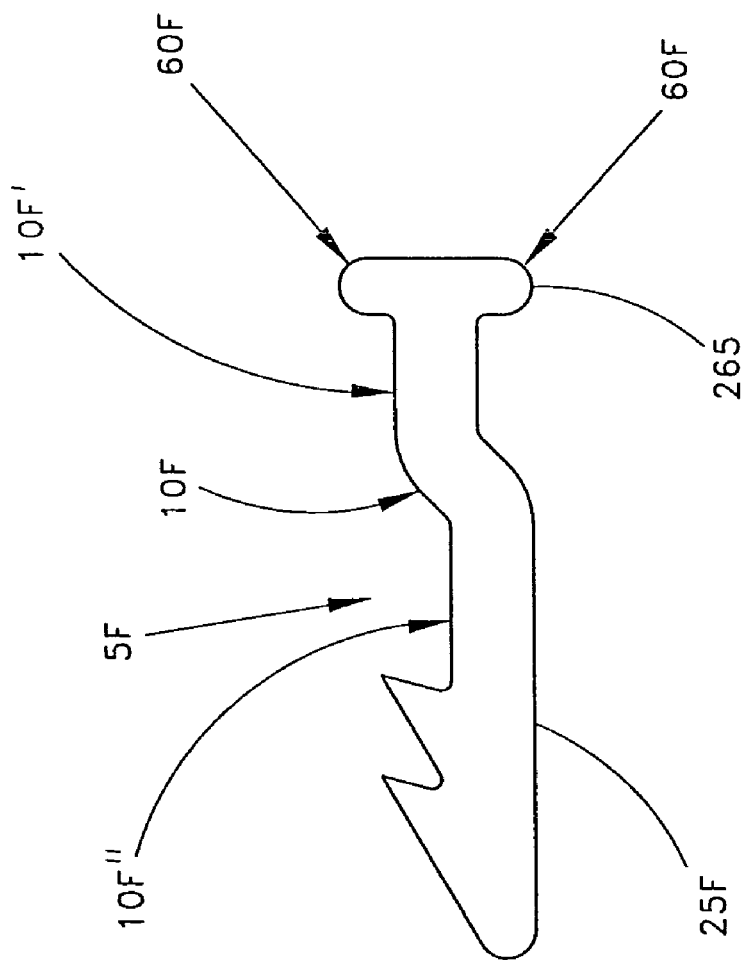
FIG. 43 is a side view of a ninth surgical fastener formed in accordance with the present invention.

FIG. 43 shows another surgical fastener 5F. Surgical fastener 5F is identical to the surgical fastener 5 described above, except that (i) the fastener's bar 60F extends on both sides of the fastener's shaft 10F, and (ii) shaft 10F has its proximal portion 10F' laterally displaced from its distal portion 10F'", so that the fastener's surface 265 is coplanar with its surface 25F. Such lateral displacement of shaft 10F at the proximal end of the shaft permits fastener 5F to fit in inserter 80, with surfaces 25F and 265 resting on inserter surface 110 (FIGS. 4 and 5).

Figure 44:
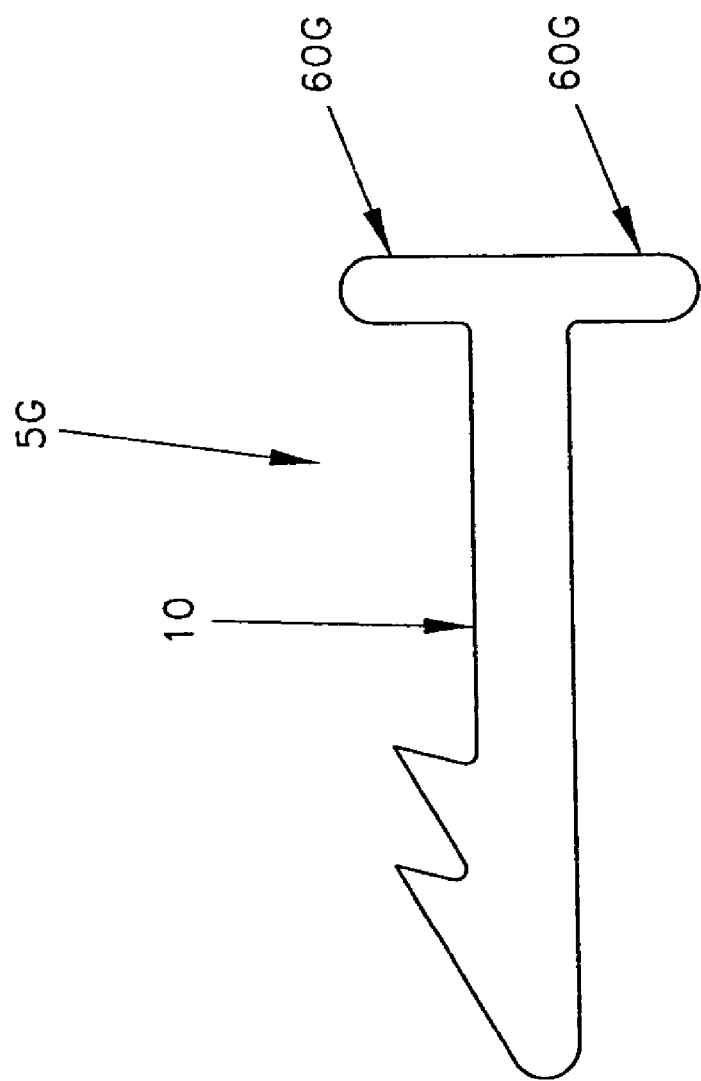
FIG. 44 is a side view of a tenth surgical fastener formed in accordance with the present invention.
Figure 45:
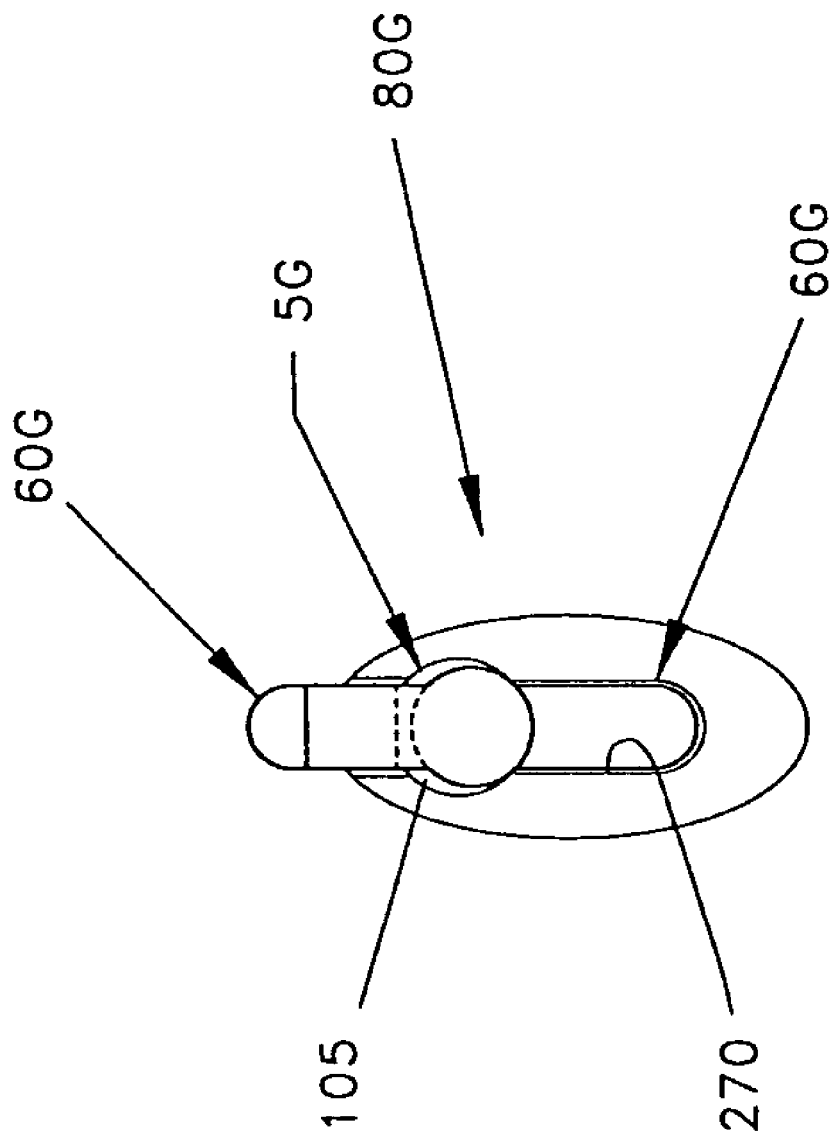
FIG. 45 is a front end view showing the tenth surgical fastener of FIG. 44 being carried by an appropriate installation tool.

FIG. 44 shows yet another surgical fastener 5G. Fastener 5G is similar to fastener 5A, except that the fastener's bar 60G extends on both sides of the fastener's shaft 10. In order to install fastener 5G in tissue, it is desirable to use an installation tool comprising an inserter 80G (FIG. 45). Inserter 80G is identical to the inserter 80 described above, except that the inserter has an elliptical cross-section, and a bottom groove 270 is disposed in the bottom surface of recess 105. Groove 270 accepts the lower portion of bar 60G.

Figure 46:
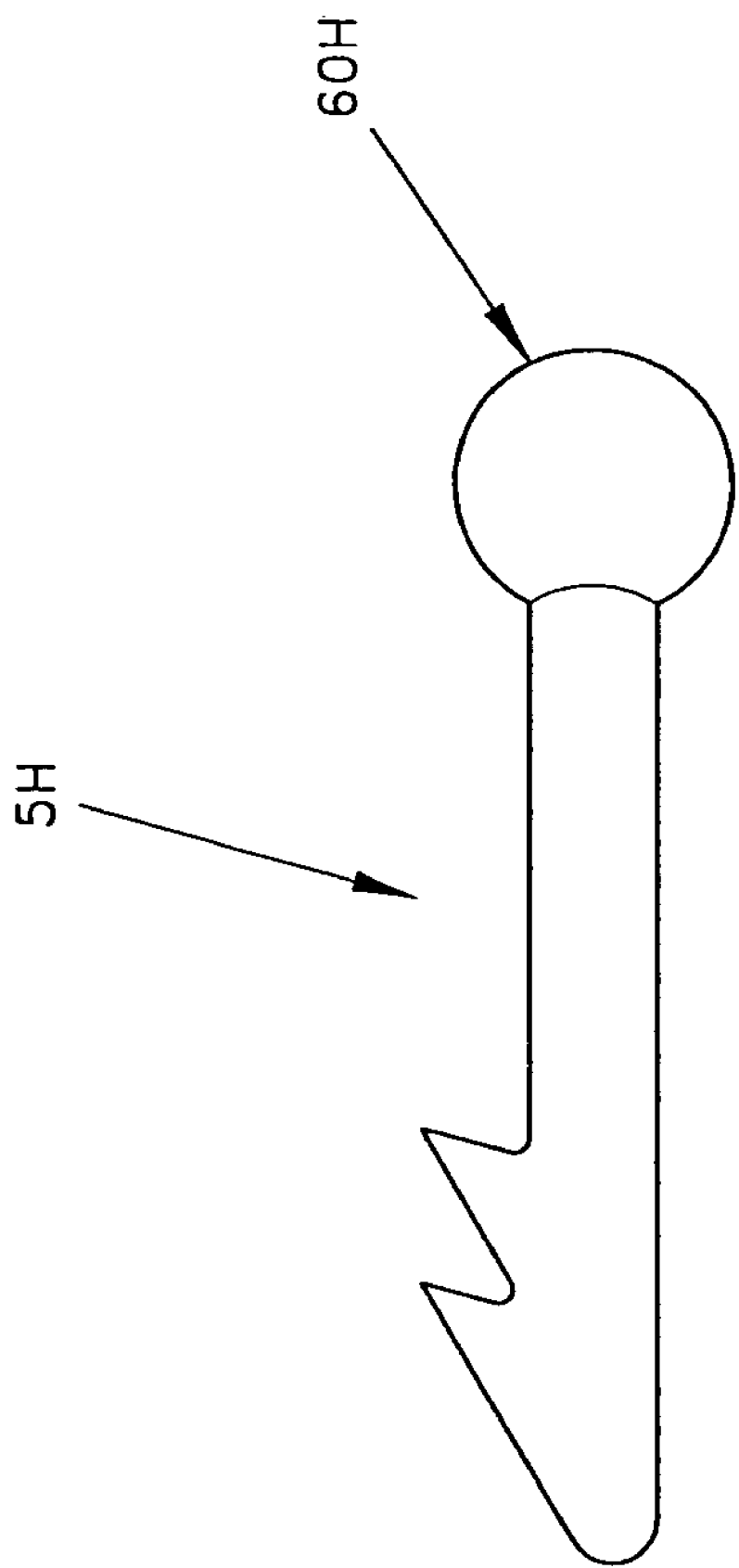
FIG. 46 is a side view of an eleventh surgical fastener formed in accordance with the present invention.

Still another surgical fastener 5H is shown in FIG. 46. Surgical fastener 5H is identical to the fastener 5G described above, except that bar 60G has been replaced with a relatively large round ball 60H. It will be appreciated that fastener 60G can be deployed into tissue using an inserter very similar to the inserter 80G shown in FIG. 45, except that the bottom groove 270 of inserter 80G would be modified so as to match the lower half of round ball 60H.

Further, while in foregoing description and drawings the surgical fastener's shaft is disclosed as having a round cross-section, other cross-sections (e.g., square or rectangular) could also be used, so long as the carrier portion of that fastener's installation tool is provided with a corresponding cross-section.

It is also to be appreciated that the present invention has utility in non-medical applications as well. Thus, for example, any one of the fasteners 5, 5A, 5B, 5C, 5D, 5E, 5F, 5G, 5H, 240 and/or 250 could be used in a non-medical setting to attach one object to another object. For example, such a fastener might be used to attach a piece of fabric to a cushion, or a planar sheet to substrate, etc.

Still other embodiments and uses of the present invention will be obvious to a person skilled in the art without departing from the scope of the present invention.

It is also to be understood that the present invention is by no means limited to the particular constructions disclosed herein and/or shown in the drawings, but also comprises any other modification, changes or equivalents within the scope of the claims.

Advantages of the Invention

Numerous advantages are obtained through the provision and use of the present invention.

For one thing, a novel surgical fastening system is provided for attaching one piece of tissue to another piece of tissue, wherein the novel surgical fastening system overcomes the various deficiencies associated with prior art surgical fastening systems.

For another thing, a novel surgical fastener is provided for attaching one piece of tissue to another piece of tissue.

And a novel installation tool is provided for deploying the aforementioned surgical fastener in tissue.

Also, a novel surgical fastening system is provided which is particularly well suited for use in repairing tears in meniscal cartilage.

And a novel surgical fastener is provided which is particularly well suited for use in repairing tears in meniscal cartilage.

Furthermore, a novel installation tool is provided which is particularly well suited for use in deploying the aforementioned surgical fastener in meniscal cartilage.

And a novel method is provided for fastening one piece of tissue to another piece of tissue.

And a novel method is provided for repairing tears in meniscal cartilage.

Still other advantages will be apparent to those skilled in the art.

What is claimed is:

1. A method for attaching one piece of tissue to another piece of tissue, the method comprising the steps of:
    providing a surgical fastener including a shaft having a bar extending therefrom at a proximal end thereof, and a fin extending therefrom proximate a distal end thereof, the bar and the fin being aligned with each other;
    providing an installation tool comprising an elongated tube having at a distal end thereof a carrier portion for releasably retaining the fastener, the carrier portion having at a distal end thereof a cutting edge and an open side portion such that the carrier portion seats the shaft therein and the bar and fin of the fastener extend through the open side portion, and control means for moving the carrier portion out of, and back into, the distal end of the elongated tube; and
    manipulating the installation tool and the control means to project the carrier portion and the fastener into the tissue and withdraw the carrier portion from the tissue, whereupon the fin resists proximal movement of the fastener through the tissue, causing the fastener to catch on the tissue such that the carrier portion can be removed from the tissue, leaving the fastener in the tissue.

2. The method of claim 1, wherein the fin projects radially outward from the fastener with a leading surface of the fin disposed at an acute angle with respect to a longitudinally axis of the fastener and a trailing surface of the fin disposed at an acute angle with respect to the longitudinal axis of the fastener, the angle of the leading surface being less than the angle of trailing surface such that the fin resists proximal movement of the fastener.

3. The method of claim 1, wherein the bar leans distally relative to the fastener such that the bar provides resistance to distal movement of the fastener through the tissue.

4. A method for attaching a first piece of tissue to a second piece of tissue, the method comprising the steps of:
    providing a surgical fastener comprising:
        a shaft;
        a bar extending radially outwardly from a proximal end of the shaft; and
        a fin extending radially outwardly from the shaft proximate a distal end of the shaft, the bar and fin being in alignment with each other along a side of the shaft;
    providing an installation tool comprising:
        an elongated rigid tube;
        a carrier portion movable between a first position in the rigid tube and a second position in which at least a part of the carrier portion extends from a distal end of the rigid tube, the carrier portion being adapted to retain the fastener and having at a distal end thereof a sharpened edge, the carrier portion seating the shaft of the fastener therein and having an open side from which extend end portions of the bar and fin; and
        control means for moving the carrier portion and the fastener therein into a body of tissue, and to withdraw the carrier portion from the tissue,
    removably connecting the fastener to the carrier portion of the installation tool, with the fin and bar of the fastener in part extending from the open side of the carrier portion, and with the distal end of the fastener disposed within the carrier portion and spaced from the edge of the carrier portion;
    placing the distal end of the rigid tube adjacent a first piece of the tissue;
    manipulating the installation tool control means to move the carrier portion distally out of the rigid tube and through the first piece of tissue and into a second piece of tissue until the bar engages the first piece of tissue; and
    manipulating the installation tool control means to move the carrier portion proximally into the rigid tube, whereupon the fin resists withdrawal of the fastener as the carrier portion is withdrawn therefrom;
    whereby to cause withdrawal of the carrier portion from the fastener, to leave the fastener in the tissue.

5. The method of claim 4, wherein the bar leans distally relative to the shaft of the fastener such that the bar provides resistance to distal movement of the fastener through the tissue such that the first piece of tissue to moved adjacent to the second piece of tissue.

6. The method of claim 4, wherein the fin includes with a leading surface disposed at an acute angle with respect to a longitudinally axis of the shaft of the fastener and a trailing surface disposed at an acute angle with respect to the longitudinal axis of the shaft of the fastener, the angle of the leading surface being less than the angle of trailing surface such that the fin resists withdrawal of the fastener.

* * * * *